(12) United States Patent
Epstein et al.

(10) Patent No.: US 7,207,969 B2
(45) Date of Patent: *Apr. 24, 2007

(54) DIRECT DUAL FILLING DEVICE FOR SEALING AGENTS

(75) Inventors: Gordon Howard Epstein, Fremont, CA (US); Mitchell E. Levinson, Pleasanton, CA (US); Richard Spero, Brentwood, CA (US); Adam Hagmann, Brentwood, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/309,338

(22) Filed: Dec. 2, 2002

(65) Prior Publication Data
US 2003/0139774 A1    Jul. 24, 2003

Related U.S. Application Data

(63) Continuation-in-part of application No. 09/307,056, filed on May 7, 1999, now Pat. No. 6,475,183.

(51) Int. Cl.
*A61M 37/00* (2006.01)
(52) U.S. Cl. .......................... 604/82; 604/240
(58) Field of Classification Search ............ 604/82–88, 604/92, 139, 181, 187, 200, 201, 205, 218, 604/232, 235, 244, 403, 407, 410–416, 191; 222/129, 80–83, 83.5, 89, 135; 206/222; 215/247, 355, DIG. 8, DIG. 3; 606/93, 214; 141/329
See application file for complete search history.

(56) References Cited

U.S. PATENT DOCUMENTS 766,202 A    8/1904    Vandewater (Continued)

FOREIGN PATENT DOCUMENTS

EP    0156098 A2    12/1984

(Continued)

*Primary Examiner*—Nicholas D. Lucchesi
*Assistant Examiner*—Laura A Bouchelle
(74) *Attorney, Agent, or Firm*—Jeffrey C. Nichols; Austin J. Foley; Joseph P. Reagen

(57) ABSTRACT

A filling device and method, particularly for two-component sealants such as fibrin sealants, which enables two fluids to be separately and directly filled to the reservoirs of a dual syringe fluid applicator from two storage containers, which can be standardized, sealed, sterilized bottles. The device has a connector which engages with the fluid applicator, is keyed to orient the applicator's fluid reservoirs in a predetermined manner and holds the containers in side-by-side alignment with the applicator. Two fluid conduits whose downward ends may be pointed to pierce seals on the bottles, extend between the applicator and the bottles and can each have a transverse reach to accommodate the girth of the bottles. The bottles may be tilted by the device to enable the conduits to draw maximal fluid from a lowermost point of the bottle. Tilting can be effected by a downward movement of the device supporting the applicator which movement can introduce the fluid conduits into the bottles. A shroud can enclose and seal the bottles and permit the apparatus complete with fluid applicator to be introduced into a sterile environment. Additionally embodiments for use with a single vial are also disclosed.

34 Claims, 20 Drawing Sheets

U.S. PATENT DOCUMENTS

| | | |
|---|---|---|
| 2,122,722 A | 7/1938 | O'Neil |
| 3,134,407 A | 5/1964 | Wegman |
| 3,405,706 A | 10/1968 | Cinqualbre |
| 3,767,085 A | 10/1973 | Cannon |
| 3,774,654 A | 11/1973 | Hjermstad |
| 3,776,700 A | 12/1973 | Gallant |
| 3,807,467 A | 4/1974 | Tascher et al. |
| 3,833,030 A | 9/1974 | Waldbauer, Jr. et al. |
| 4,092,546 A * | 5/1978 | Larrabee ............... 250/515.1 |
| 4,128,098 A | 12/1978 | Bloom et al. |
| 4,325,913 A | 4/1982 | Wardlaw |
| 4,359,049 A | 11/1982 | Redl et al. |
| 4,434,820 A | 3/1984 | Glass |
| 4,505,709 A * | 3/1985 | Froning et al. ............ 604/411 |
| 4,552,277 A | 11/1985 | Richardson et al. |
| 4,607,671 A * | 8/1986 | Aalto et al. ............... 141/329 |
| 4,629,455 A | 12/1986 | Kanno |
| 4,690,165 A | 9/1987 | Leytes et al. |
| 4,810,123 A | 3/1989 | Bruggeman |
| 4,856,567 A | 8/1989 | Cosmai |
| 4,883,483 A | 11/1989 | Lindmayer |
| 4,902,281 A | 2/1990 | Avoy |
| 4,969,669 A | 11/1990 | Sauer |
| 4,978,336 A | 12/1990 | Capozzi et al. |
| 5,116,315 A | 5/1992 | Capozzi et al. |
| 5,163,433 A | 11/1992 | Kagawa et al. |
| 5,171,146 A | 12/1992 | Guerci |
| 5,171,214 A * | 12/1992 | Kolber et al. ............... 604/82 |
| 5,195,985 A | 3/1993 | Hall |
| 5,226,877 A | 7/1993 | Epstein |
| 5,297,561 A | 3/1994 | Hulon |
| 5,314,412 A * | 5/1994 | Rex ........................... 604/191 |
| 5,329,976 A | 7/1994 | Haber et al. |
| 5,344,417 A * | 9/1994 | Wadsworth, Jr. ........... 604/414 |
| 5,364,386 A * | 11/1994 | Fukuoka et al. ........... 604/411 |
| 5,364,387 A * | 11/1994 | Sweeney .................... 604/411 |
| 5,368,563 A | 11/1994 | Lonneman et al. |
| 5,405,607 A | 4/1995 | Epstein |
| 5,445,631 A | 8/1995 | Uchida |
| 5,454,409 A * | 10/1995 | McAffer et al. ........... 141/329 |
| 5,478,323 A * | 12/1995 | Westwood et al. .......... 604/191 |
| 5,582,596 A | 12/1996 | Fukunaga et al. |
| 5,585,007 A | 12/1996 | Antanavich et al. |
| 5,591,143 A | 1/1997 | Trombley, III et al. |
| 5,605,255 A | 2/1997 | Reidel et al. |
| 5,605,541 A | 2/1997 | Holm |
| 5,612,050 A | 3/1997 | Rowe et al. |
| 5,648,265 A | 7/1997 | Epstein |
| 5,656,035 A | 8/1997 | Avoy |
| 5,759,169 A | 6/1998 | Marx |
| 5,759,171 A | 6/1998 | Coelho et al. |
| 5,788,662 A | 8/1998 | Antanavich et al. |
| 5,827,262 A * | 10/1998 | Neftel et al. ................ 604/414 |
| 5,893,397 A * | 4/1999 | Peterson et al. .............. 141/27 |
| 5,901,883 A | 5/1999 | Ritsche |
| 5,935,437 A | 8/1999 | Whitmore |
| 5,971,956 A | 10/1999 | Epstein |
| 5,989,215 A | 11/1999 | Delmotte et al. |
| 6,003,566 A * | 12/1999 | Thibault et al. .............. 141/25 |
| 6,063,297 A | 5/2000 | Antanavich et al. |
| 6,253,804 B1 * | 7/2001 | Safabash ...................... 141/97 |
| 6,475,183 B1 * | 11/2002 | Epstein et al. ................ 604/82 |
| 6,488,650 B1 * | 12/2002 | Epstein et al. ................ 604/82 |

FOREIGN PATENT DOCUMENTS

| | | |
|---|---|---|
| EP | 0302411 B1 | 6/1992 |
| EP | 0738498 A1 | 10/1996 |
| EP | 0156098 B1 | 11/1998 |
| WO | WO 8904676 | 6/1989 |
| WO | WO 9001959 | 3/1990 |
| WO | WO 9406487 | 3/1994 |
| WO | WO 9629113 A1 | 9/1996 |
| WO | WO 9725015 | 7/1997 |
| WO | WO 9728834 A1 | 8/1997 |
| WO | WO 9807846 A1 | 2/1998 |
| WO | WO 9846300 A1 | 10/1998 |
| WO | WO 99/17833 * | 4/1999 |
| WO | WO 9917833 A1 | 4/1999 |
| WO | WO 9930769 | 6/1999 |
| WO | WO 9932155 | 7/1999 |
| WO | WO 9939642 A1 | 8/1999 |
| WO | WO 9962588 A1 | 12/1999 |

* cited by examiner

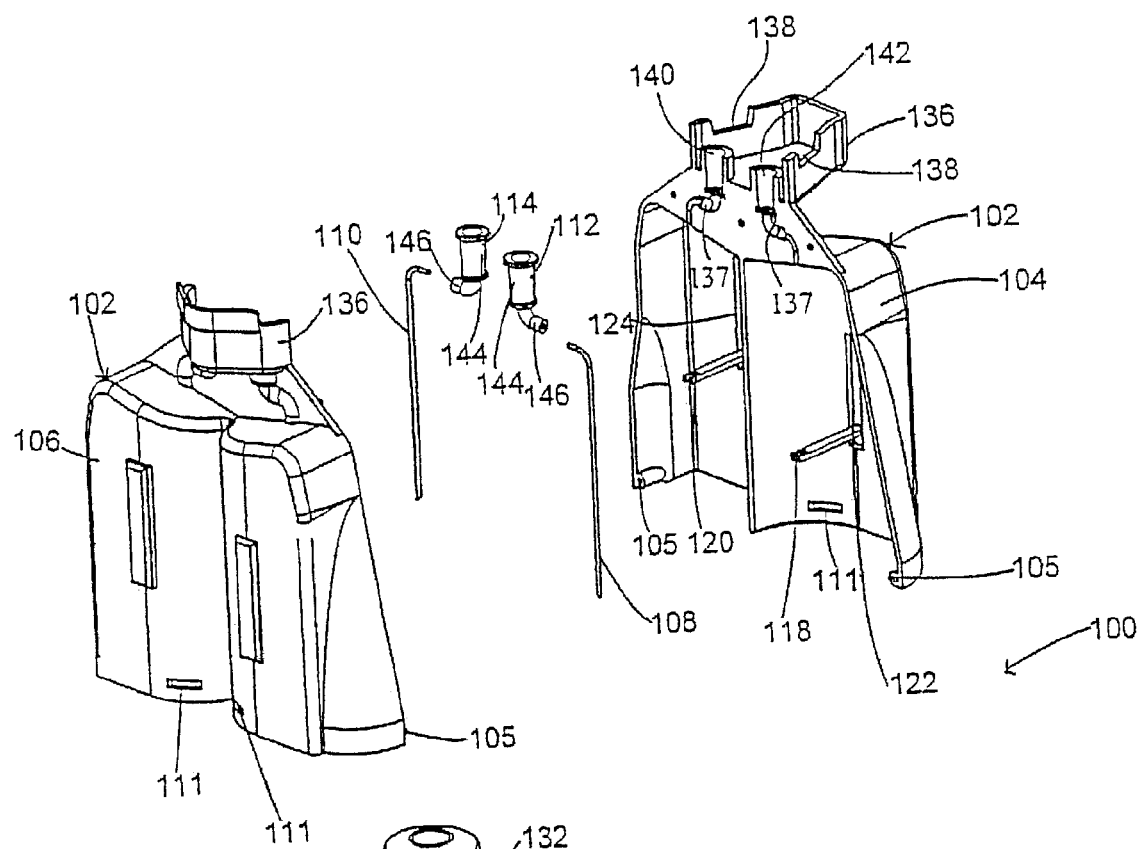
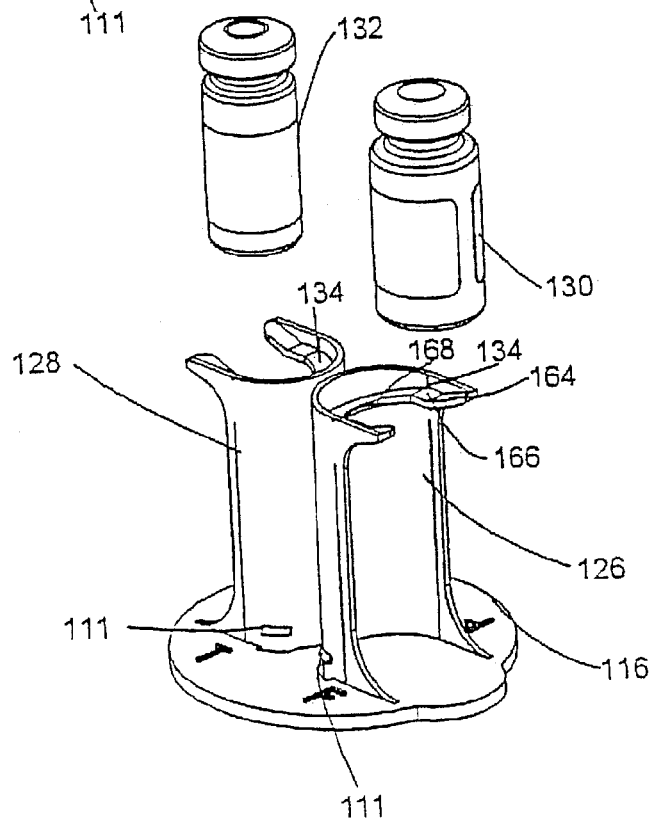
FIG. 7

DIRECT DUAL FILLING DEVICE FOR SEALING AGENTS

CROSS REFERENCE TO RELATED APPLICATIONS

This application is a continuation-in-part of copending U.S. patent application Ser. No. 09/307,056, filed on May 7, 1999, to Epstein et al, now issued U.S. Pat. No. 6,475,183, the subject matter of which is hereby incorporated by reference. This application discloses subject matter related to our U.S. patent application Ser. No. 08/838,078, now issued U.S. Pat. No., 6,331,172, and Ser. No. 08/839,614, now issued U.S. Pat. No. 5,971,956, both filed Apr. 14, 1997, to patent application Ser. No. 08/946,364 filed Oct. 7, 1997, now issued U.S. Pat. No. 6,007,515, and to patent application Ser. No. 09/037,160 filed Mar. 9, 1998, now issued U.S. Pat. No. 6,063,055, all naming Gordon H. Epstein as first inventor. The disclosures of the aforementioned United States patent applications, "the above applications" are hereby incorporated herein by reference thereto.

BACKGROUND OF THE INVENTION

1. Field of the Invention

The present invention relates to a filling device for an applicator which applies multiple fluid sealant components to a work surface and is particularly, although not exclusively, useful for applying tissue sealant components to biological tissue to effect hemostasis or achieve other therapeutic results. More particularly, it relates to a dual compartment enclosed direct filling device for a hand-held applicator.

2. Description of Related Art Including Information Disclosed under 37 CFR 1.97 and 37 CFR 1.98

Use of tissue sealants and other biological materials is an important emerging surgical technique, well adapted for the operating room or field environments such as the doctor's office or mobile medical units. Preferred sealants include fibrin sealants which are formed from blood plasma components and comprise, on the one hand, a first component containing fibrinogen and Factor XIII and on the other hand a second component which usually includes thrombin, and calcium ions. The fibrinogen is capable of a polymerizing and being cross-linked to form a solid fibrin clot when the components are mixed. The necessary additional factors to simulate relevant portions of the natural blood coagulation cascade are suitably distributed between the fibrinogen and thrombin components.

Antanavich et al. U.S. Pat. No. 5,585,007, whose disclosure and references are hereby incorporated herein by reference thereto, provides an extensive discussion of the literature relating to fibrinogen sealant preparation (column 1, line 20 to column 4, line 62) and applicators column 4 line 62 to column 5, line 14), as well as a bibliography, (columns 6–10) and is a helpful guide to the teachings of prior workers in the field.

Depending upon the potency of the particular formulations employed, coagulation of the sealant may take place very rapidly, yielding a gel within perhaps 10 or 20 seconds. Though often very desirable for surgical reasons, such fast-acting properties present potential problems of fouling or clogging. These problems must be overcome in devising suitable applicators, methods of application and devices suitable for filling said applicators.

A popular manually operable applicator for such two-component sealants employs a dual syringe construction wherein two syringes, connected by a yoke, each provide a reservoir for one of the components. In most prior devices, the sealant components are discharged in separate streams and mixed externally of the applicator. Such applicators are similar in principle to household epoxy glue applicators commonly available in hardware stores.

Until May of 1998, when the FDA first approved such products, fibrin sealant was not commercially available in the US, therefore use of fibrin sealant was limited to supplies produced within the clinic, which are not subject to FDA control.

Current methods of filling biological glue applicators can be complicated and time consuming. As taught in Epstein U.S. Pat. No. 5,266,877 and in our assignee's international application PCT/US98/07846, components of the sealant can be placed in separate compartments in a flat filler tray for transfer to an applicator. Though useful as a device to permit rapid and reliable filling of a dual syringe applicator at the point of use, such filler trays are not suitable for external storage of the sealant components. This process can be time consuming and it requires a significant degree of care to efficiently transfer the sealant to the applicator. Also, a small amount of sealant will be left in the tray, and it is thus wasted. Furthermore the transfer of sealant components to multiple storage containers raises the likelihood in which the sealants will gather bio-burden, and bacteria, which can threaten the sterility of the sealant.

After FDA approval, however, fibrin sealant is now commercially available in the US. This availability has created a need for an effective and efficient device useful for transferring the components of the sealant, from commercially available or standardized, bottle-like storage containers, into an applicator.

There is accordingly a need for a device which can effectively deliver, in a sterile environment, multiple sealant components directly from their storage containers to an applicator.

SUMMARY OF THE INVENTION

The present invention solves the problem of effectively delivering multiple sealant components directly from commercially available or standardized storage containers, for example, bottles, to an applicator while allowing the use of the entire fill device within a sterile field.

In one aspect, the invention provides a direct dual filling device for the multiple sealant components of a liquid sealant, at least two of said components being complementary one to the other and polymerize when mixed, the direct filling device comprising a body having a plurality of inlet ports connected to drawing tubes which pierce the protective covering of commercially available bottles, the bottles containing the sealant components. The device also having a hood which snaps onto a base thereby enclosing the bottles. within the structure, allowing the device to be brought into a sterile field. The base having slanted bottle supports which hold the bottles in a tilted position. This feature allows the drawing tubes to extract virtually all of the fluid contained within the bottles. The device can be attached to an applicator with keying such that when the plunger of the applicator is retracted, fluid is drawn from each respective bottle to the proper reservoir contained within the applicator. Applications are disclosed for use with single vials.

The invention enables multiple sealant components to be directly delivered from their commercially available containers into an applicator without significant risk of contamination of the sealant components, and with minimal wasting of the sealant components. The different sealant components are delivered directly from their containers into separate individual reservoirs, thereby preventing coagulation of the sealant components. Once the hood of the device is guided onto the bottles and snapped onto the base, the entire device can be brought into the sterile environment.

BRIEF DESCRIPTION OF THE DRAWINGS

One way of carrying out the invention is described in detail below with reference to the drawings which illustrate one or more specific embodiments of the invention and in which:

FIG. 7 is an exploded view of an alternative embodiment of the present invention;

DESCRIPTION OF THE PREFERRED EMBODIMENTS

Figure 1:
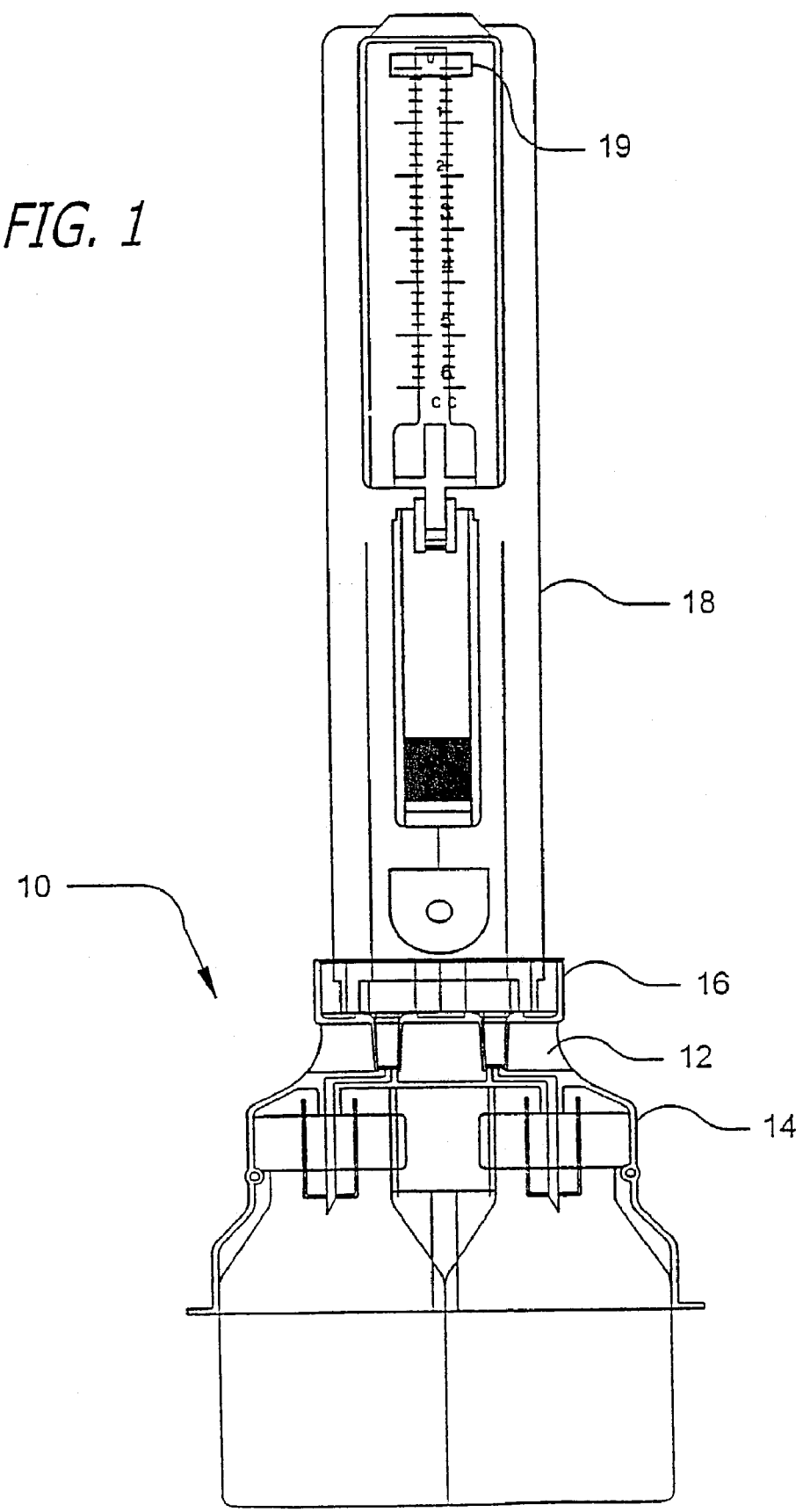
FIG. 1 is a side elevational view of a direct dual filling device connected to an applicator according to the present invention.
Figure 2:
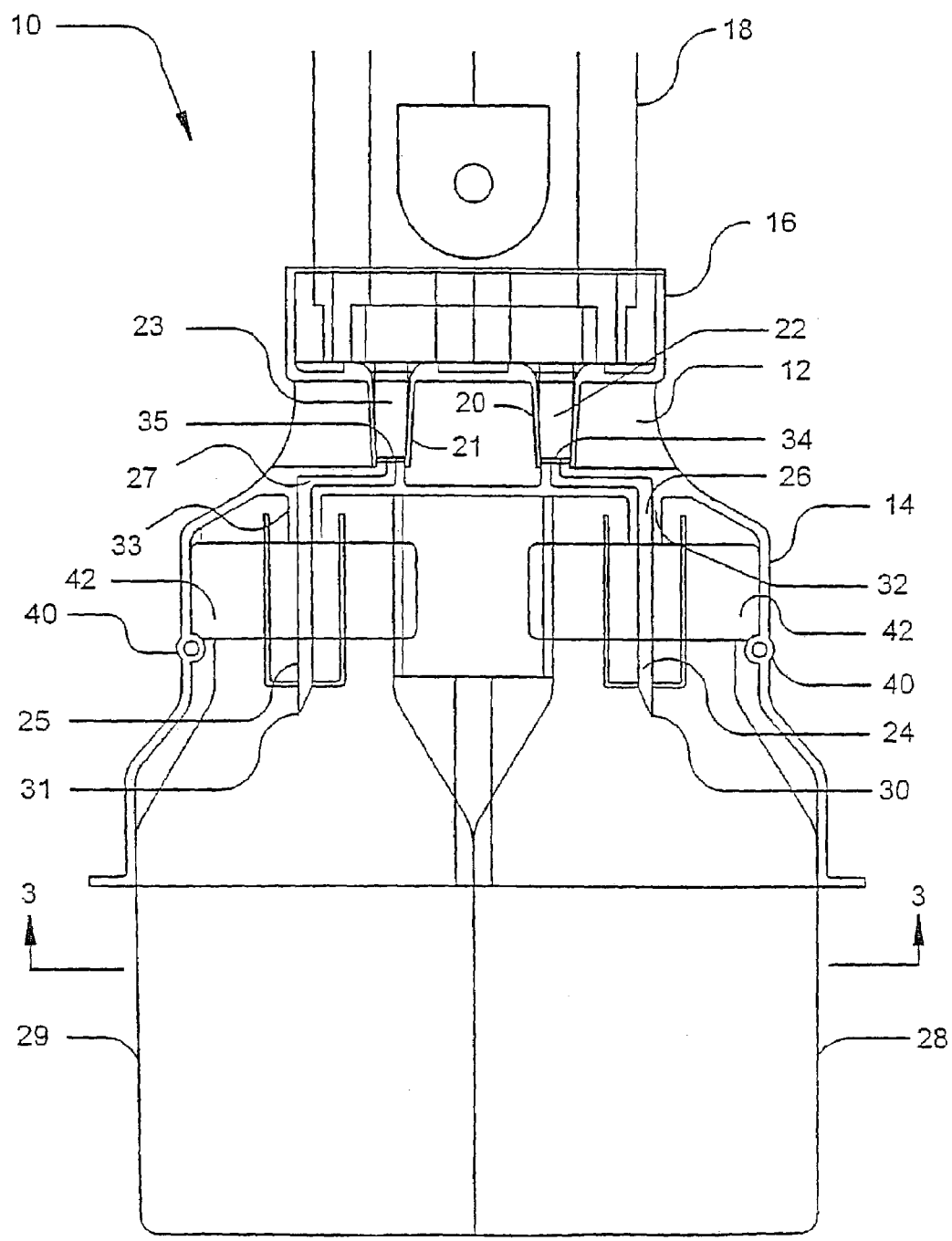
FIG. 2 is an enlarged side elevational view of the present invention.

Referring to FIGS. 1 and 2 of the drawings, the direct dual filling device 10 comprises a body 12, a hood 14 and a collar 16 which is adapted to fit an applicator 18. The inventive device is preferably constructed out of a clear thermoplastic material such as polycarbonate, polystyrene, polypropylene, polytetrafluoroethylene, acrylonitrile butadiene-styrene or acrylic, however any suitable material may be used.

Applicator 18 preferably has at least two fluid reservoirs for separately holding and controllably dispensing reactable fluids, each of the fluid reservoirs being connected to a syringe by a fluid conduit. The applicator is of the type primarily used for applying multiple fluid sealant components to biological tissue to effect hemostasis or achieve other therapeutic results.

However the inventive filling device can be adapted to fit applicators having a wide variety of uses which require the direct filling of fluids into separate reservoirs located within an applicator.

Located within body 12 are inlet ports 20 and 21 which are adapted to receive syringes 22 and 23 of applicator 18. Rubber O-rings 34 and 35 are positioned within inlet ports 20 and 21 respectively, such that an air tight seal is formed. Inlet ports 20 and 21 are connected to drawing tubes 24 and 25 by transverse channels 26 and 27 respectively, which drawing tubes 24 and 25 extend into bottles 28 and 29.

Drawing tubes 24 and 25 should have sufficient length to extract substantially all the liquid contained within the bottle, or conversely they should have a length such that when the system is inverted substantially all of the liquid can be extracted. Drawing tubes 24 and 25 are preferably configured with pointed ends 30 and 31 which have the ability to pierce the protective packaging found on standard medical fluid bottles 28 and 29 and form a seal. Drawing tubes 24 and 25 are preferably formed out of a metallic material, however any suitable material such as thermoplastic may be used. The tubes can also have the ability to be removed from support sleeves 32 and 33 for replacement.

Channel 26 allows the fluid contained within right bottle 28 to be drawn through tube 24 and into syringe 22 for deposit within the proper receptacle located within applicator 18 without coming into contact with the fluid contained within bottle 29. Similarly, channel 27 allows the fluid contained within left bottle 29 to be drawn through tube 25 and into syringe 23 for deposit within the proper receptacle located within applicator 18 without coming into contact with the fluid contained within bottle 28. This allows the simultaneous filling of both sides of the applicator directly from the commercially available containers. Channels 26 and 27 can be formed out of thermoplastic tubing or molded directly into body 12 of the direct filling device 10.

Figure 3:
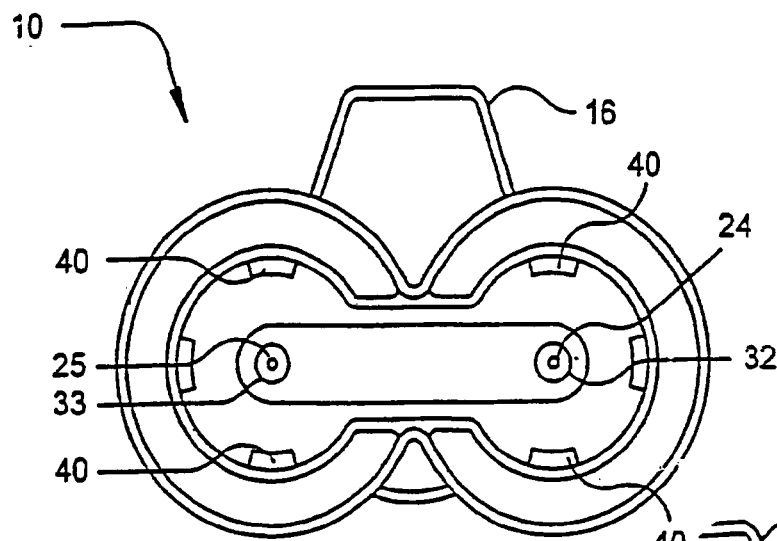
FIG. 3 is a view of the present invention along section lines 3—3 of FIG. 2.
Figure 3A:
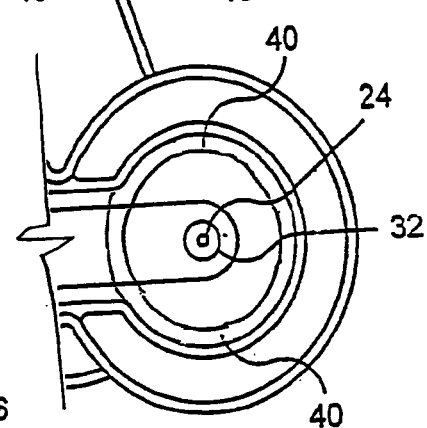
FIG. 3A is a view similar to FIG. 3 showing an alternate embodiment wherein the hood includes a locking member which comprises an o-ring.

In order to fill applicator 18 directly from bottles 28 and 29, hood 14 is placed over said bottles such that pointed tips 30 and 31 are approximately centered on the protective seal covering the bottles. The contoured shape of hood 14 guides the inventive device as the bottles are seated and snap into place within hood 14 by locking members 40. As clearly shown in FIG. 3, locking members 40 are located within hood 14 such that they move apart when cap 42 of its respective bottle passes by during the insertion of the bottle, then once the bottle has reached the proper location locking members 40 retract under bottle cap 42 to lock or "seat" the bottles in place. Once the bottles have been seated the system may be inverted to ensure that all of the fluid is draw out of the bottles. In FIG. 3A, an alternate locking member 40A is illustrated showing the locking members comprising an o-ring which extends radially inward from the hood.

The plunger 19 of applicator 18 is then retracted thereby drawing the fluid contained within bottles 28 and 29 through their respective drawing tubes and channels into the syringes of applicator 18 for deposit within a reservoir.

Figure 4:
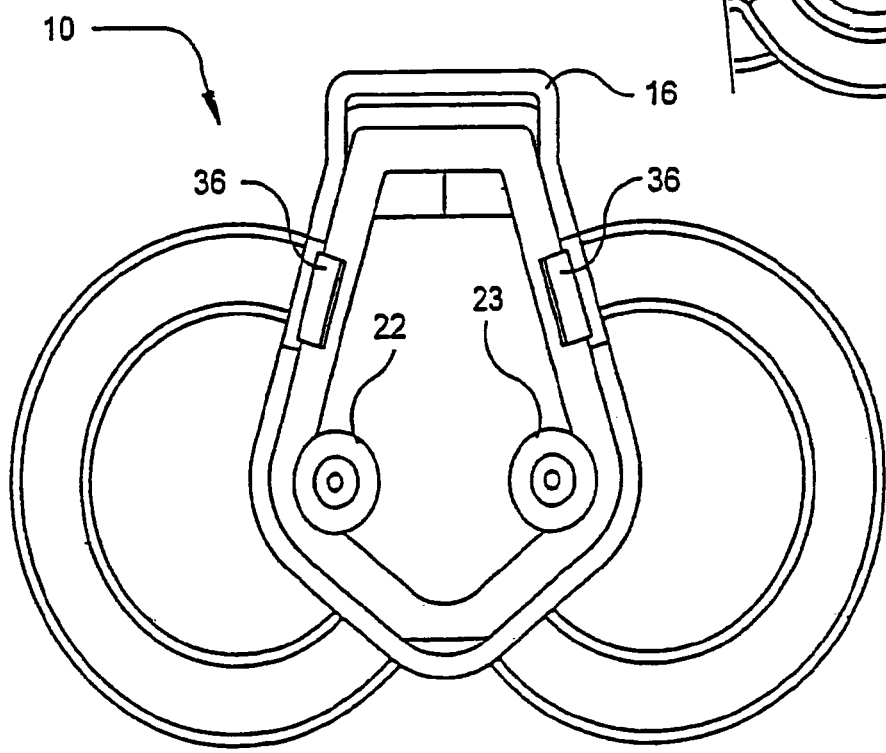
FIG. 4 is a top view of the present invention.
Figure 5:
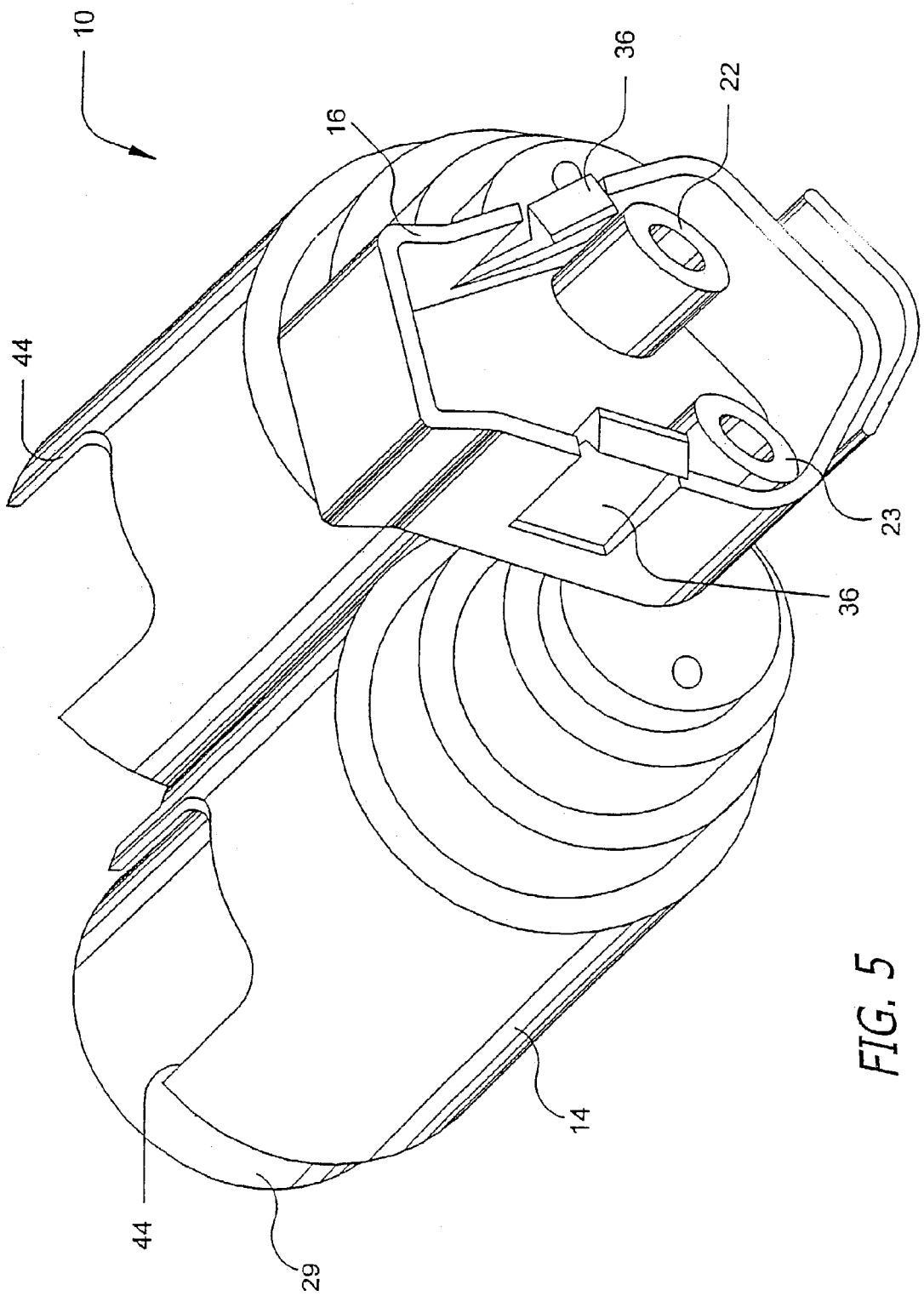
FIG. 5 is a perspective view of the present invention.

The direct filling device 10, as shown in FIG. 4, is connected to applicator 18 by a pair of snap fit members 36. Applicator 18 is placed over the filling device such that the syringes are approximately centered over inlet ports 22 and 23, then pressed down until locked in place by snap fit members 36. The novel shaping of the collar 16 allows filling device 10 to mate with applicator 18 in only one orientation, thereby "keying" the fill device to the applicator. The general pentagon shape precisely fits to the applicator body in the same manner as interchangeable applicator tips or heads, which are used for droplet or spray dispensing of sealant. This feature of keying the filling device collar to the applicator ensures the proper fibrin components are delivered to their respective reservoirs without significant risk of cross-contamination, particularly when refilling. The agent bottles can only fit into the fill device hood 14 one way and the applicator can As depicted in FIG. 5, bottle 29 is inserted into hood 14 until seated by locking members 40. As can be clearly seen, hood 14 has a recess 44 which aides the user in removal of the bottles. Recess 44 is also useful, if hood 14 is opaque, to view any labels present on the bottle so it can be verified that the proper components are delivered into the proper reservoirs. Also shown is the contoured shape of hood 14. The shape can be varied to allow use of different types and shapes of bottles. The hood can also be modified so that each side allows insertion of a different shaped bottle, thereby keying the bottles to the fill device. This in conjunction with the novel shape of the collar is important in ensuring that the proper components are delivered to the proper reservoirs within the applicator.

The direct dual filling device embodiment shown in FIGS. 6–11 is a more detailed embodiment of the invention which includes most of the features shown in the embodiment of FIGS. 1–5 and is suitable for manufacturing from injected molded plastics components. As will be described, several of the parts of the direct dual filling device shown in FIGS. 6–11 embody similar construction and functionality to the components of the embodiment shown in FIGS. 1–5.

Figure 6:
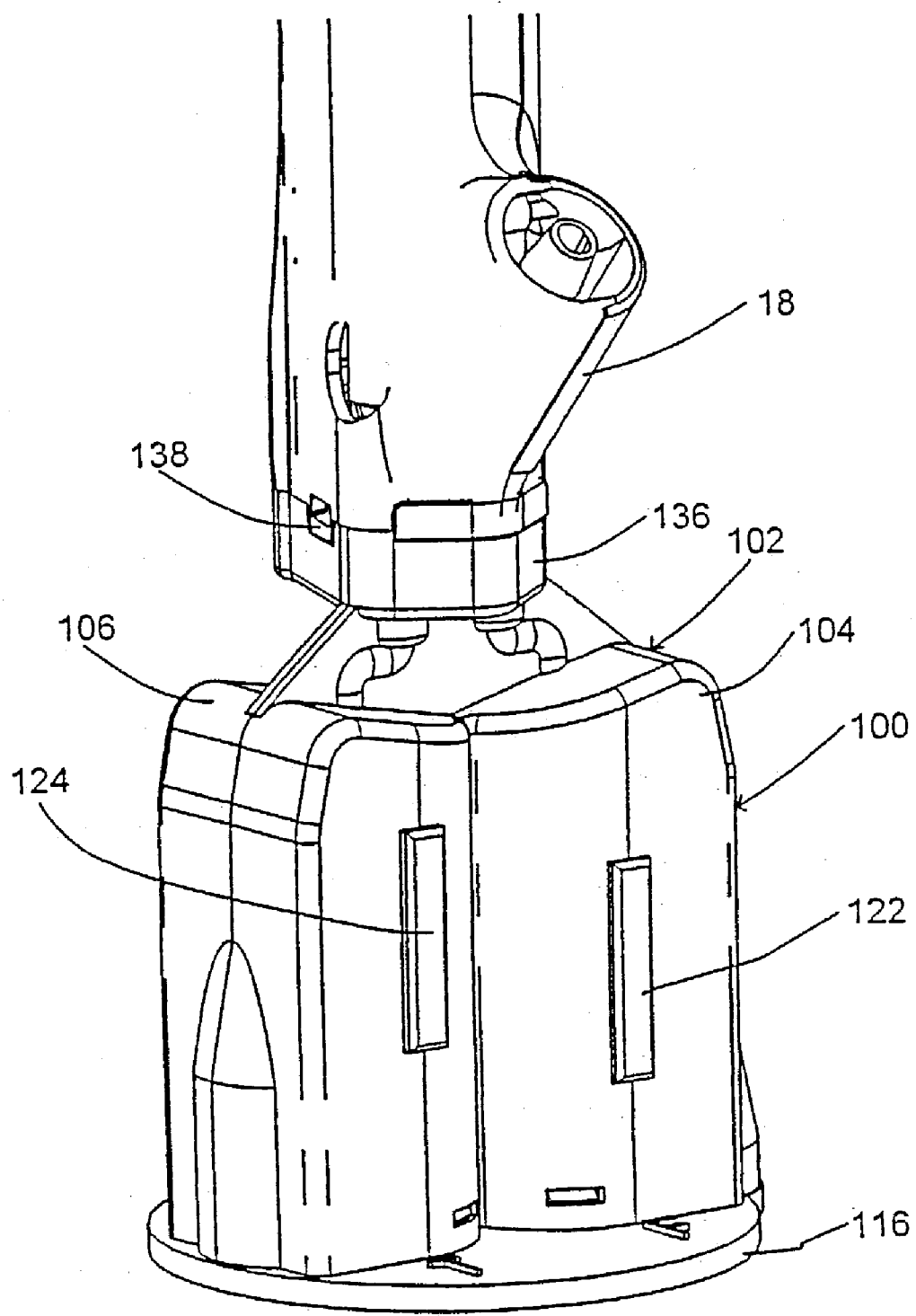
FIG. 6 is a perspective view of a direct dual filling device connected to an applicator according to an alternative embodiment of the present invention.

Many individual structural features of the components of the direct dual filling device can be seen from the exploded view of FIG. 7, while FIGS. 8–13 show additional structural features and relationships of the internal components and FIG. 6 shows the overall external appearance of the direct tool filling device while in use.

Referring to FIG. 7, the direct dual filling device 100, shown in exploded view, comprises a hood 102, having a first half 104 and a second half 106, a pair of drawing tubes 108 and 110, a pair of fluid conduits 112 and 114, and a base 116. First-half 104 and second half 102, of hood 102 have a pair of drawing tube guides 118 and 120, and a pair of recesses 122 and 124. Base 116 has a pair of vial supports 126 and 128 which are configured to support vials 130 and 132. Additionally, each of the vial supports 126 and 128 have a vial support surface 134.

Hood 102 can be contoured to resemble the shape of the filling device when assembled with agent vials. The shape can also vary to allow use of different types and shapes of bottles. The hood can be modified so that each side allows insertion of a different shaped bottle, thereby keying the bottles to the fill device. This in conjunction with the novel shape of the collar is important in ensuring that the proper components are delivered to the proper reservoirs within the applicator.

In preferred embodiments, hood 102 and base 116 are essentially rigid, injected molded components having limited resilience in their thinner sections. Hood 102 is also preferably formed from a clear plastic such as polycarbonate or SAN. In contrast, fluid conduits 112 and 114 are preferably fabricated from a distinctly elastomeric, resilient molding material such as silicone rubber.

Once assembled hood 102 is configured to snap into the base by use of snap fit members 111. Hood 102 and base 116 are configured such that they may only be assembled in one direction, so in use, the operator cannot assemble the device incorrectly. Base 116 and hood 102 are also color-coded to indicate which side is for the thrombin vial in which side is for the fibrinogen vial. Furthermore, base 116 is labeled with a "T" indicating the side for thrombin, and an "F" indicating the side for fibrinogen once hood 102 is snapped onto base 116, bottles 108 and 110 can be brought into the sterile field.

When assembled, the upper portions of first-half 104 and second half 106 combine to form a collar 136, embodying features of collar 16. A pair of channels 137 having inlet ports 140 and 142 are also defined within hood 102. Channels 137 are configured to retain fluid conduits 112 and 114.

Fluid conduits 112 and 114 comprise a cylindrical cup 144 and a tubular arm 146, which fits suitably within channel 137. Cups 144 are internally configured to be pressed into tight sealing engagement, when so mounted to syringes 22 and 23 of applicator 18, with the ends of sealant components syringes mounted in a mating applicator body, to receive liquid components therefrom. Tubular arms 146 of fluid conduits 112 and 114 are flexible and can readily be manipulated during assembling of filling device 102. The ends of tubular arms 146 are configured to be fitted with the ends of drawing tubes 108 and 110 respectively. This configuration allows liquid components to be drawn through tube 108 into fluid conduit 112 and stored within the respective reservoir located within applicator 18. Similarly, liquid component may be drawn through tube 110 into fluid conduit 114 and stored within the other reservoir located within applicator 18 without significant risk of contamination. When assembled, the filling device provides an airtight interface from the drawing tubes to the applicator reservoir.

Drawing tubes 108 and 110 should have sufficient length to extract substantially all the liquid contained within the corresponding vial. Drawing tubes 108 and 110 are preferably configured with a pointed end which has the ability to pierce the protective seal found on standard medical fluid bottles thereby forming a seal. Drawing tubes 108 and 110 generally resemble a needle, and are preferably formed out of a metallic material, however any suitable material such as thermoplastic may be used. Both of the tubes may be of similar diameter, however the tube diameter may differ to accommodate liquids having differing viscosities.

Figure 13:
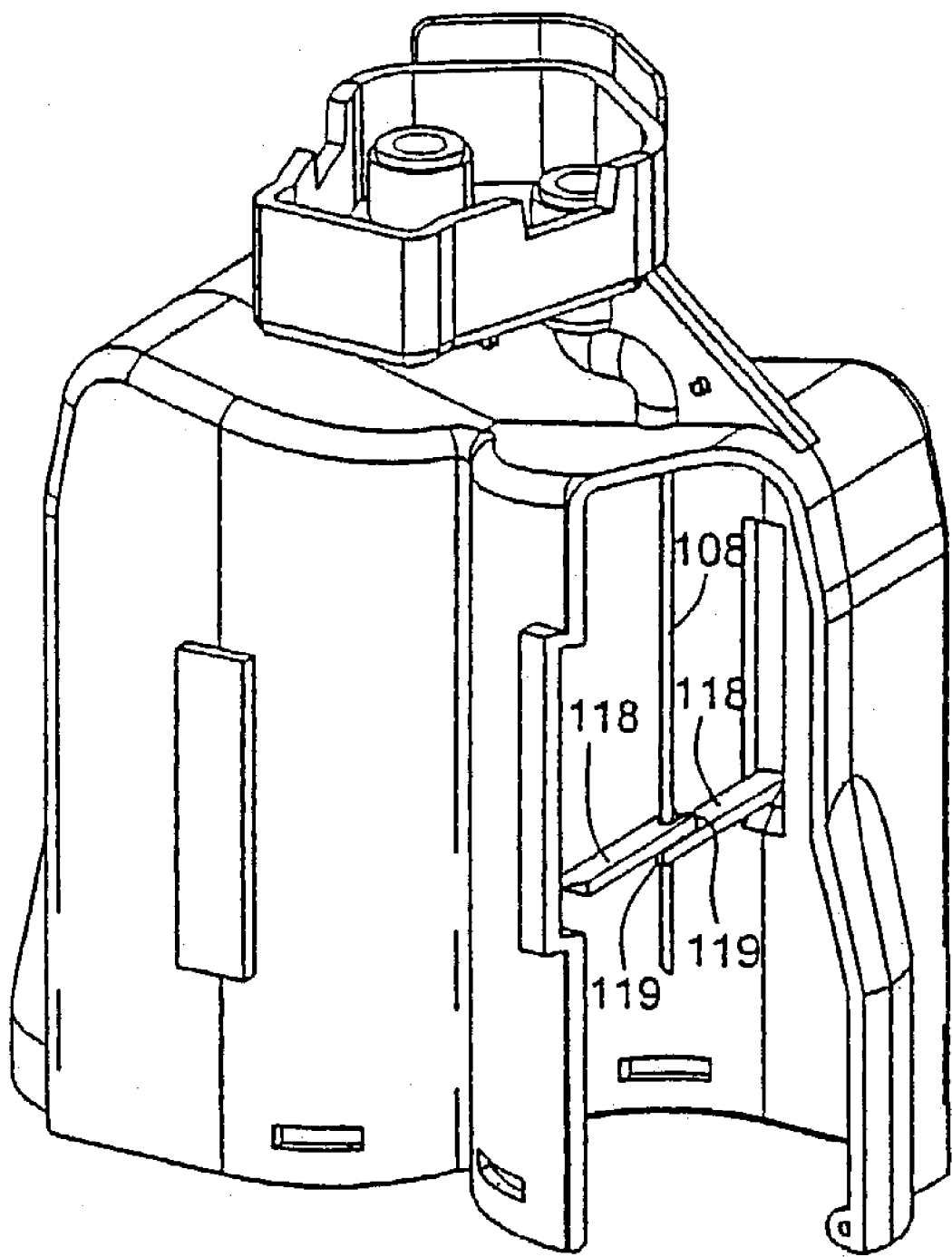
FIG. 13 is a cut away view showing the drawing tube held in place by the guide

Drawing tube guides 118 and 120 are hinged within recesses 122 and 124 so that they may be housed within the recesses when the filling device used in use. FIG. 13 illustrates the manner in which drawing to 108 is held in place by drawing tube guides 118. Each of the guides has a forked end 119 which when used in conjunction with one another will hold drawing tube 118 in a vertical position. Recesses 122 and 124 should be of suitable size to allow for variations in the position of the guide, when it is being stored.

Collar 136 is connected to an applicator 18 by a pair of snap fit members 138. Applicator 18 is placed over direct dual filling device 100 such that the syringes of applicator 18 are approximately centered over inlet ports 140 and 142, then pressed down until in place by snap fit members 138. Alternatively, collar 136 may be configured without snap fit members 138. Due to the stability of the device when assembled, applicator 18 can be held in place by a combination of gravity and the friction generated by the tight nature of the seal formed between the syringes and the fluid conduits. The novel shaping of collar 136 allows direct dual filling device 100 to mate with applicator 18 in only one orientation, thereby "keying" the fill device to the applicator. The general pentagon shape precisely fits the applicator body in the same manner as interchangeable applicator tips or heads, which are used for droplet or spray dispensing of sealant. This feature of keying the filling device collar to the applicator insures the proper fibrin components are delivered to their respective reservoirs without significant risk of cross-contamination, and the resulting loss of materials caused by the cross-contamination.

Figure 8:
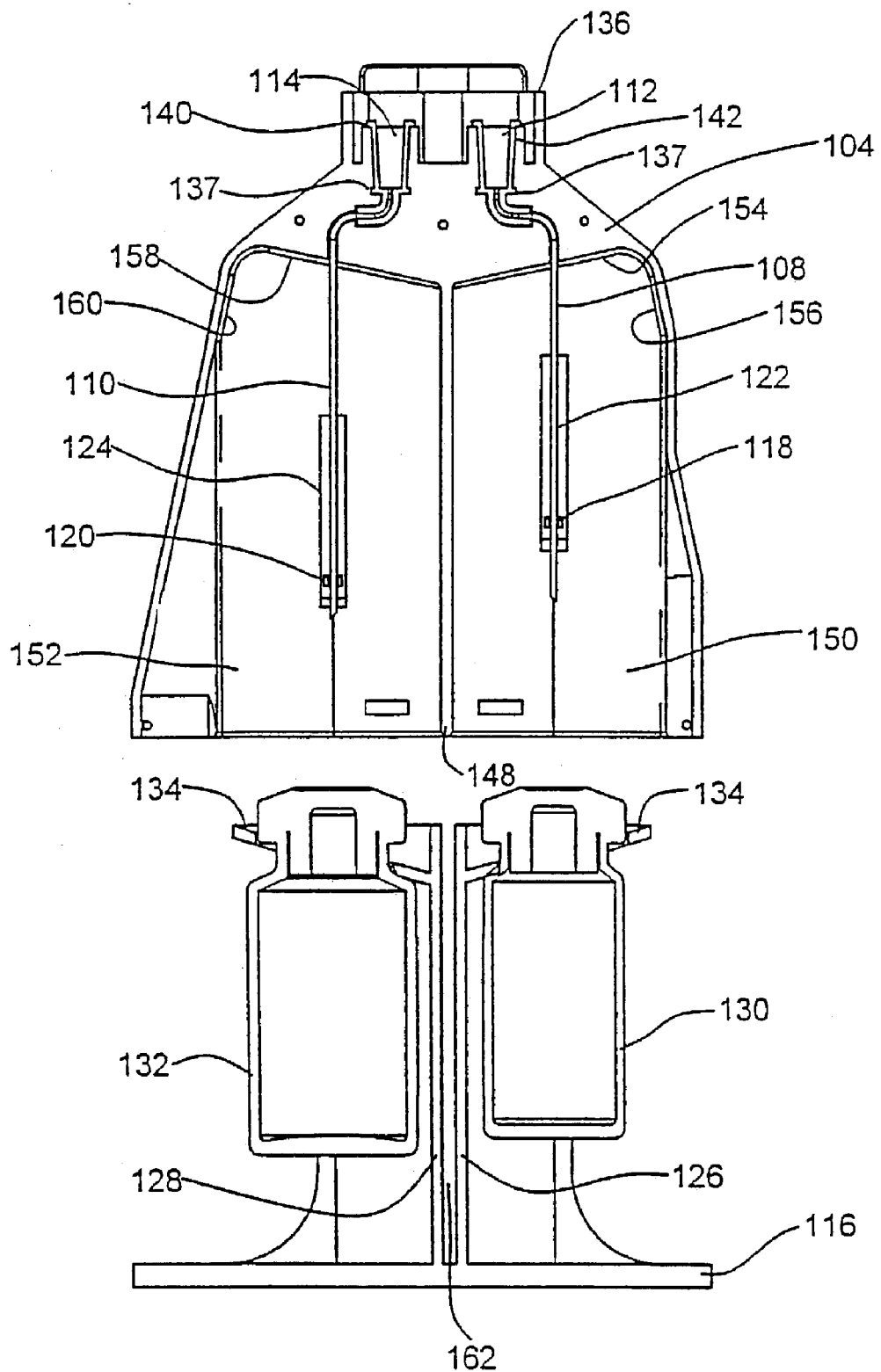
FIG. 8 is an elevational section view of an alternative embodiment of the present invention.

As shown in FIG. 8, first-half 104 of hood 102 has a central divider 148 which divides the hood into two compartments 150 and 152, which when hood 102 is assembled, house vials 130 and 132 respectively. Compartment 150 has an upper surface 154 which is slanted from its lowest point at divider 148 to its highest point at outer wall 156. Similarly, compartment 152 has an upper surface and 158 which is slanted from its lowest point at divider 148 to its highest point at outer wall 160.

Vial supports 126 and 128 are separated by divider slot 162 which is configured to receive central divider 148 of hood 102. Vial support surface 134 has a slanted outer portion 164, a level central portion 166, and an inner slanted U-shaped surface 168. The angle at which the inner and outer portions of vial support surface 134 is constructed, is substantially parallel to slanted upper surface 154 and 158 of hood 102. Vial support surface 134 has a width which allows vials 130 and 132 to be suspended by their necks as shown in FIG. 8.

The assembly of the components of filling device 100 can take place at a factory or other such manufacturing facility prior to use of the inventive device. Drawing tubes 108 and 110 are mated with tubular arms 146 of fluid conduits 112 and 114. The assembly is then snugly fitted within channel 137 such that drawing tubes 108 and 110 all are held by guides 118 and 120 respectively. Preferably, one half of channel 137 is of sufficient proportion to accommodate a greater portion of fluid conduits 112 and 114. This allows the fluid conduits to be placed within the larger channel prior to be two halves being assembled, thereby allowing for greater restraint of the conduits prior to assembling the two halves of hood 102.

Once the drawing tubes and fluid conduits are in place, first-half 104 and second-half 106, of hood 102 are configured to be assembled together by snap fit members 105. Alternatively, ultrasonic welding, glue, press fitting or any other method of assembly may be used. All of the components of the inventive device are then sterilized. When it is desired to use the inventive filling device the operator need only insert the vials and mate the hood onto the base.

Generally, the agent vials are not sterilized and are unable to be brought into a sterile environment without risk of contamination. However, when the agent vials are shrouded within the inventive filling device the assembly may be brought into a sterile environment for use.

The operator assembles the device by sliding the agent vials onto vial supports 126 and 128 such that the necks of the two agent vials are resting on vial support surface 134. The angle at which the outer portion 164 of vial support surface 134 is configured, will cause the two agent vials to slide down into place resting on level central portion 166 of vial support surface 134. The angle is such that friction will not stop the bottle from fully seating on level central portion 166. As shown and FIG. 10 a vial 130 is properly seated within vial support 126 when the center line 180 of vial 130 is positioned at a point on level central portion 166 further out than pivot fulcrum 182. Pivot fulcrum 182 occurs at the point where level portion 166 transforms into inner support surface 168. This positioning allows vial 130 to be firmly held in place by support 126, while still allowing vile 130 to pivot in the direction of arrow 184. By allowing vial 130 to fully seat within vial support surface 134, vial 130 will maintain a level position during the first part of the insertion of the drawing tube. This allows the needle to properly align with the target area of the vials septum. Since the vials septum has a thin portion in be center which allows needles to puncture, it is desirable to align the drawing tube with this target area, thereby assuring a good seal.

Figure 9:
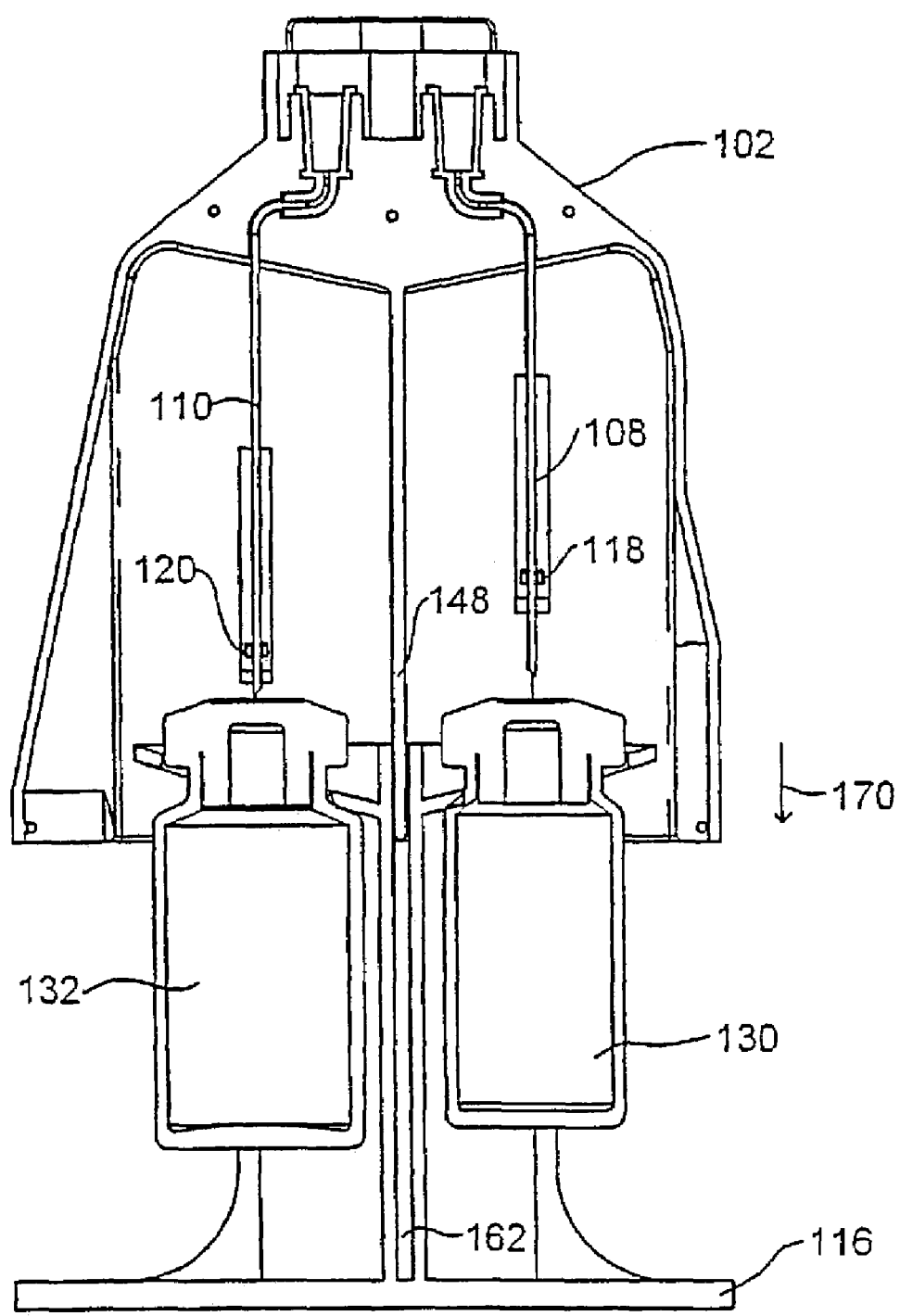
FIG. 9 is an elevational view of an alternative embodiment of the present invention.

Once the vials are properly seated, the hood assembly is placed over the base assembly such that divider 148 is positioned to engage within divider slot 162 as shown in FIG. 9. As the hood assembly is lowered onto the base in the direction of arrow 170, divider 148 and divider slot 162 act to align drawing tubes 108 and 110 with the target area of agent vials 130 and 132.

As the hood assembly is further lowered onto the base in the direction of arrow 170, drawing tubes 108 and 110 puncture the septa of the agent vials creating an airtight interface. As indicated earlier the drawing tubes should be held vertical by their guides and the agent vials positioned correctly by the vial support face so that the drawing tubes puncture the target area of the septa.

Figure 12:
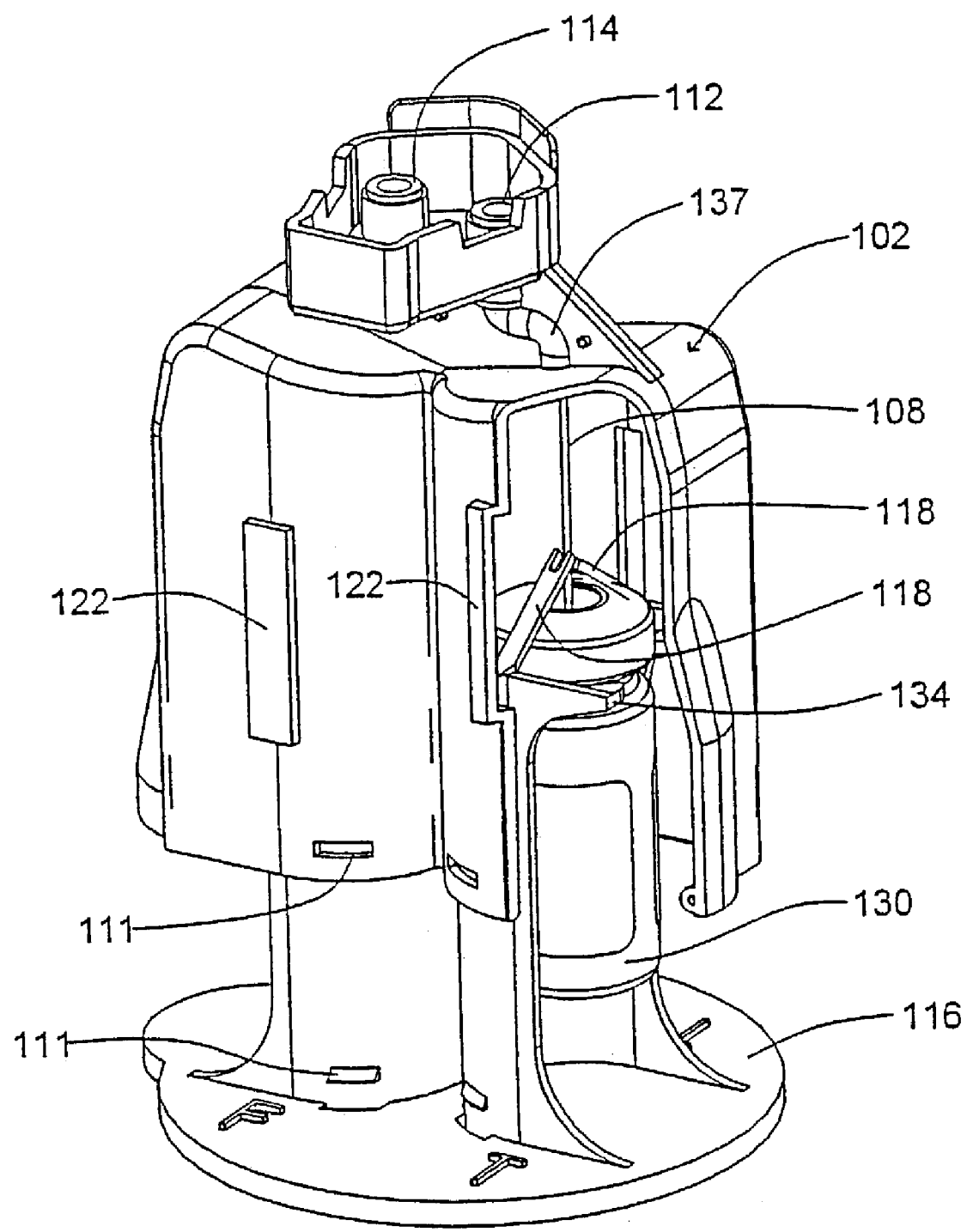
FIG. 12 is a cut away view showing the hood being lowered onto the base during assembly.

As illustrated in FIG. 12, when guides 118 and 120 come into contact with the top portion of agent vials 130 and 132 they all are folded up and out of the way into recesses 122 and 124.

Figure 10:
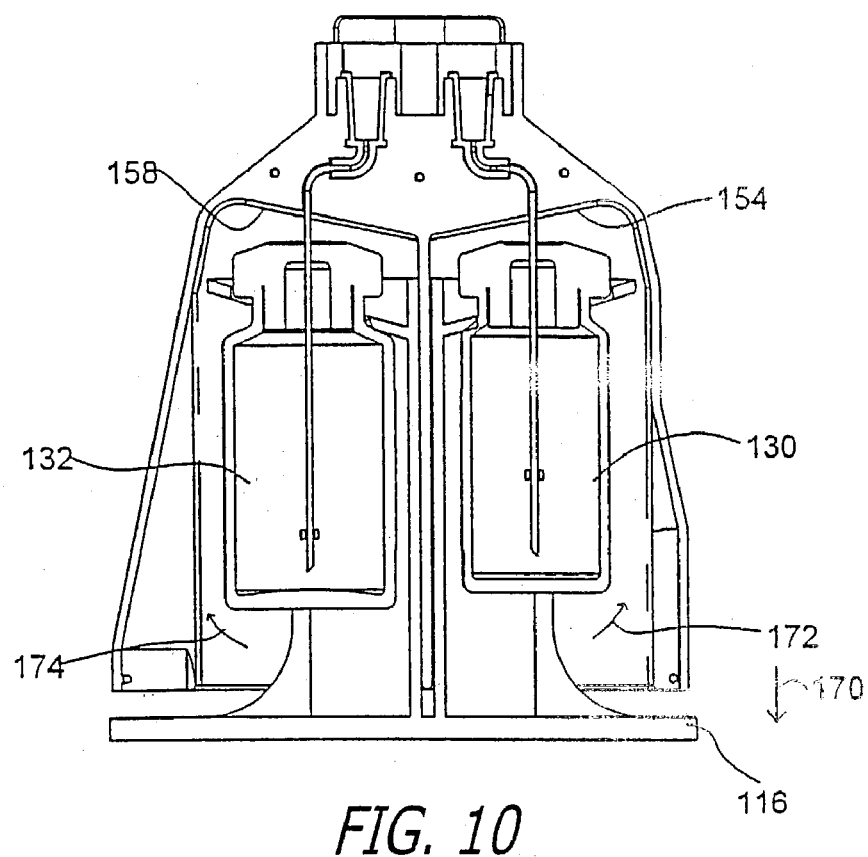
FIG. 10 is an elevational view of an alternative embodiment of the present invention.
Figure 10A:
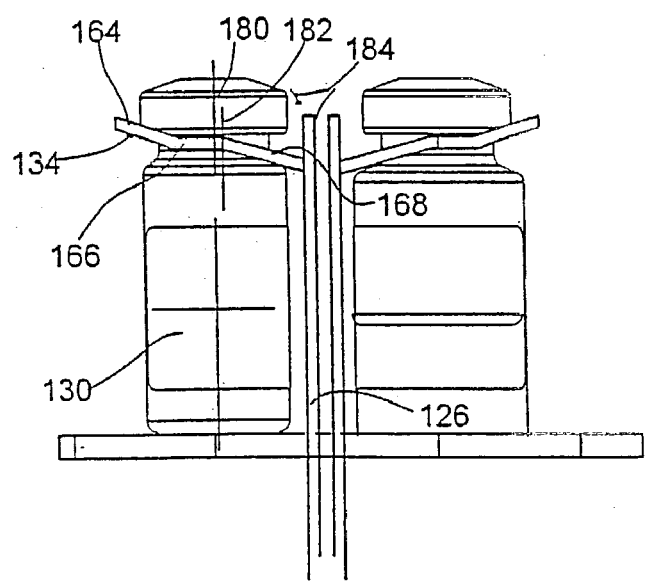
FIG. 10a is a partial elevational view depicting the vial support.

FIG. 10 depicts the point at which the top portion of vials 130 and 132 comes into contact with upper surfaces 154 and 158. As the housing moves onto the base in the direction of arrow 170, the slanted configuration of upper surface 154 causes agent vial 130 to tilt in the direction of arrow 172. Similarly, the slanted configuration of upper surface 158 causes agent vial 132 to tilt in the direction of arrow 174. The vials are tilted because the top slanted inner surface of the housing vial cavities are forced down onto the lid of each vial, causing them to tilt to the same angle as the top of the inner cavity.

Simultaneously with the tilting of agent viles 130 and 132, drawing tubes 108 and 110 are driven into the bottom corner of their respective viles. Ideally, the sharpened tips of the drawing tubes are shaped such that they conform to the shape of the bottom corner of the agent vials so that as much fluid as possible is drawn up.

Figure 11:
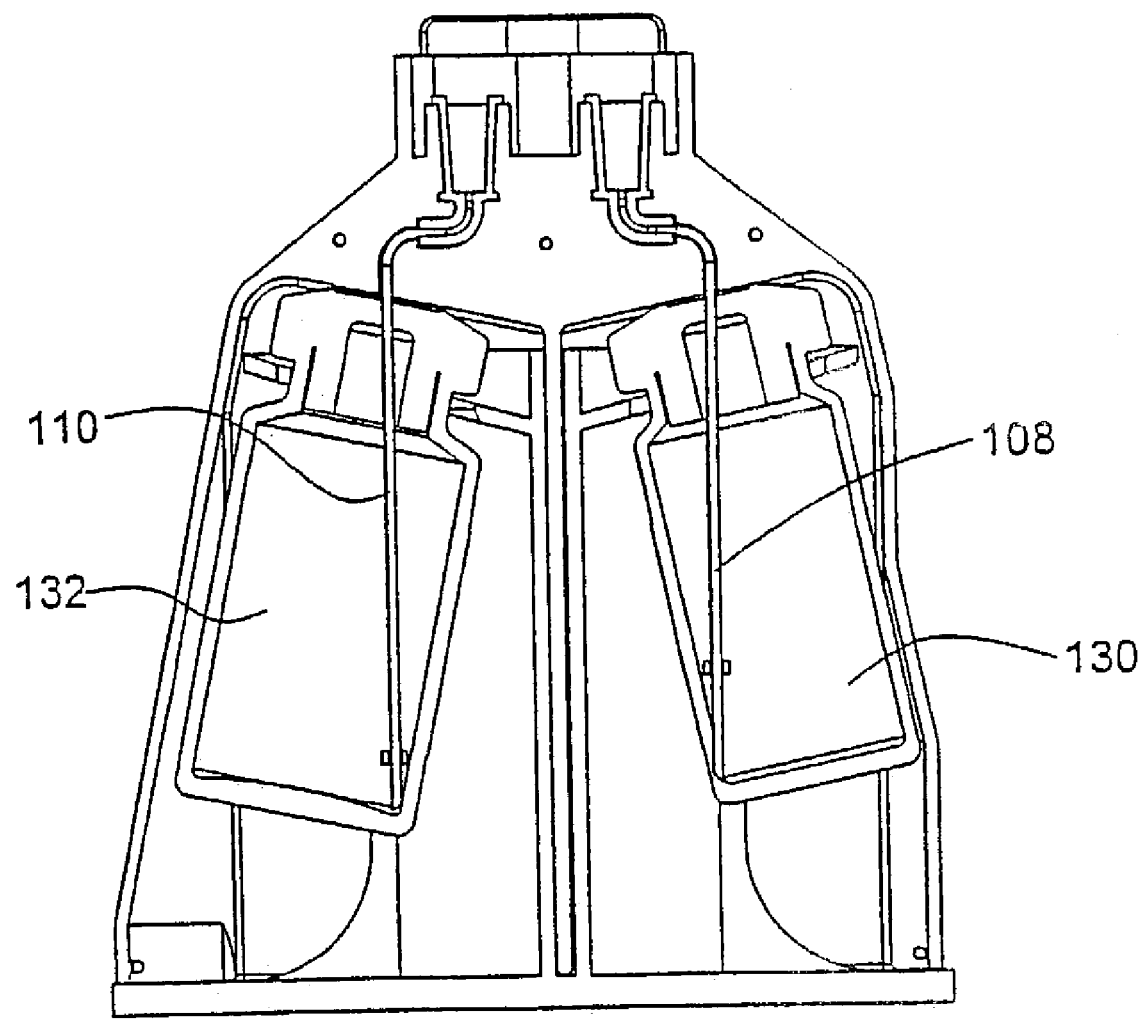
FIG. 11 is an elevational view of an alternative embodiment of the present invention.

Once the hood assembly has been completely lowered onto the base into the fully engaged position of FIG. 11, it may be locked into place by snap fittings 111. Agent vials 130 and 132 are tilted in such a manner that drawing tubes 108 and 110 are forced into the bottom corner of each respective vial, which has now become the low point for the agent to pool into. This configuration along with the shaping of the drawing tubes allows for minimal waste of the agent contained within the vials.

Once the inventive filling device is assembled, it may be brought into a sterile field. Although, the agent vials are generally not sterile and therefore would not be allowed within a sterile environment for risk of contamination, the hood and base assembly has effectively shrouded the vials within a sterile environment so that they may be brought into a sterile field.

Figure 14:
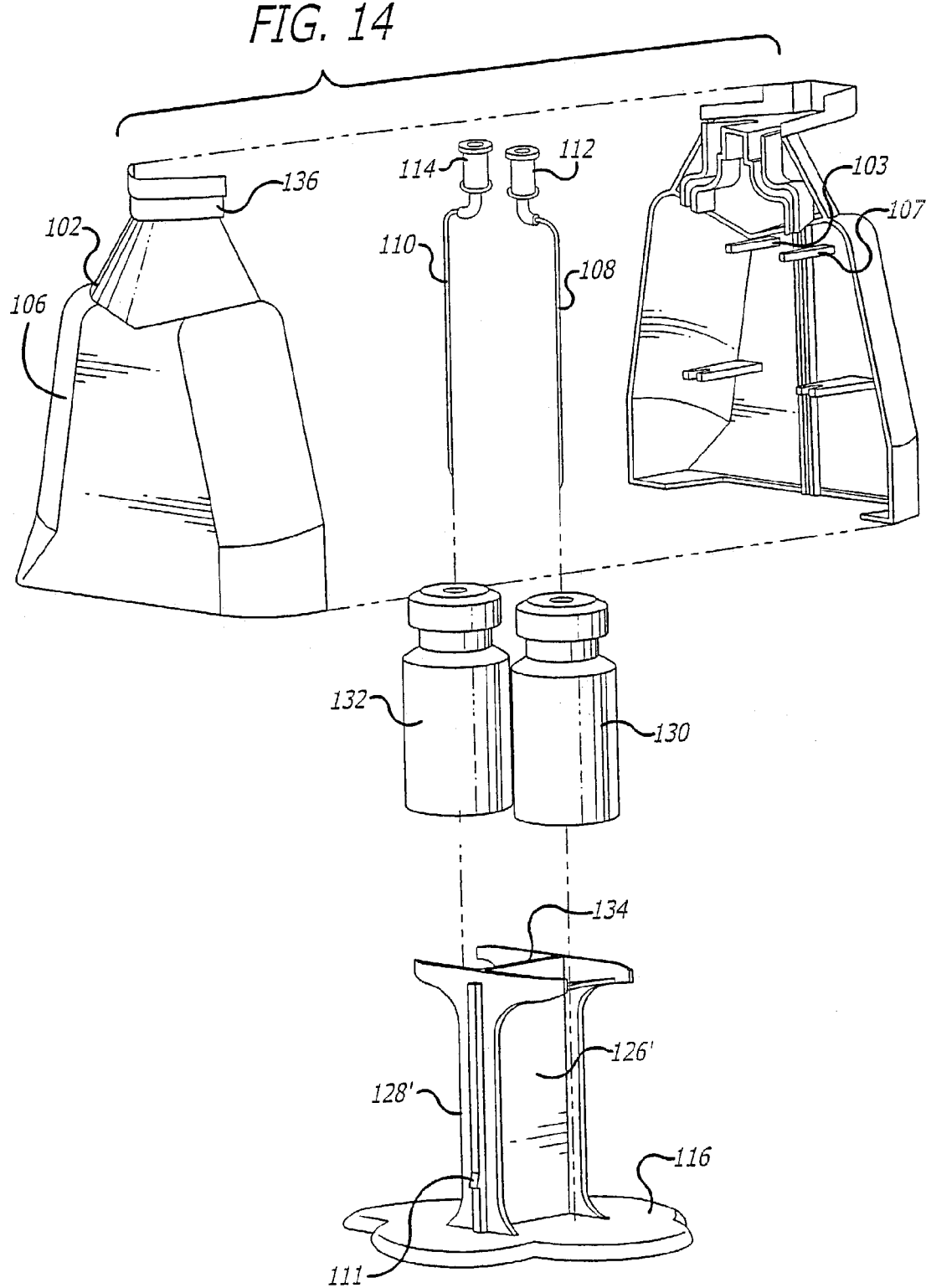
FIG. 14 is an exploded view showing an alternative embodiment of the hood.
Figure 15:
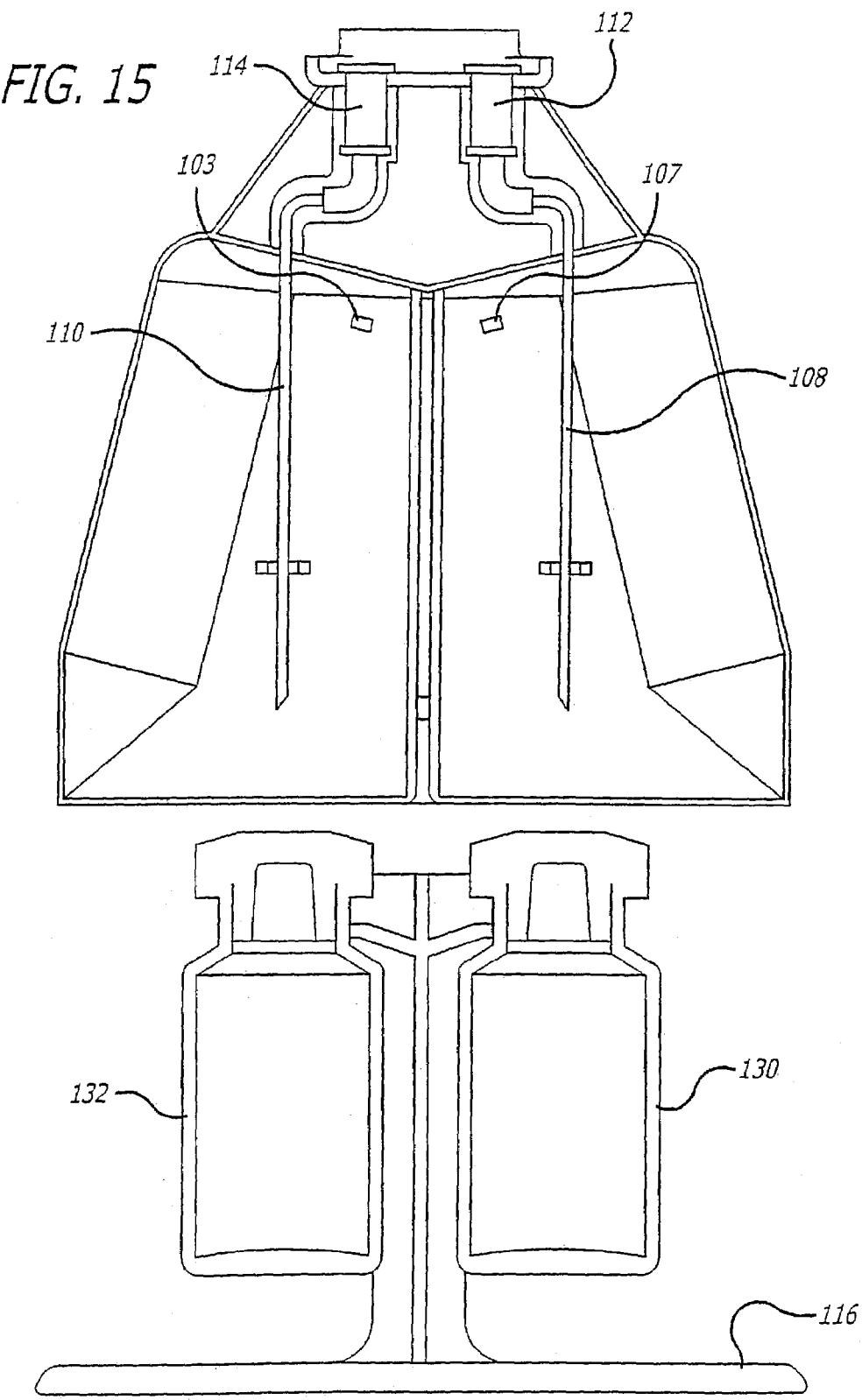
FIG. 15 is an elevational section view of the embodiment shown in FIG. 14.

FIGS. 14–17 show an alternative embodiment of the inventive device. Referring to FIGS. 14 and 15, hood 102 comprises compliant upper arms 103 and 107 which act as compliant tipping arms. Arms 103 and 107 are vertically positioned and have a resilient flexibility to engage and tip vials 130 and 132 as hood 102 is lowered before the needles bottom out on the vials' convexity and hold vials 130 and 132 in tilted position so as to optimize evacuation of the contents of vials 130 and 132. Base 116 comprises modified vial supports 126' and 128' which are open on either side of vials 130 and 132. Thus, a nurse or other user may load a device without touching the base thus avoiding contaminating the sterile field.

Figure 16:
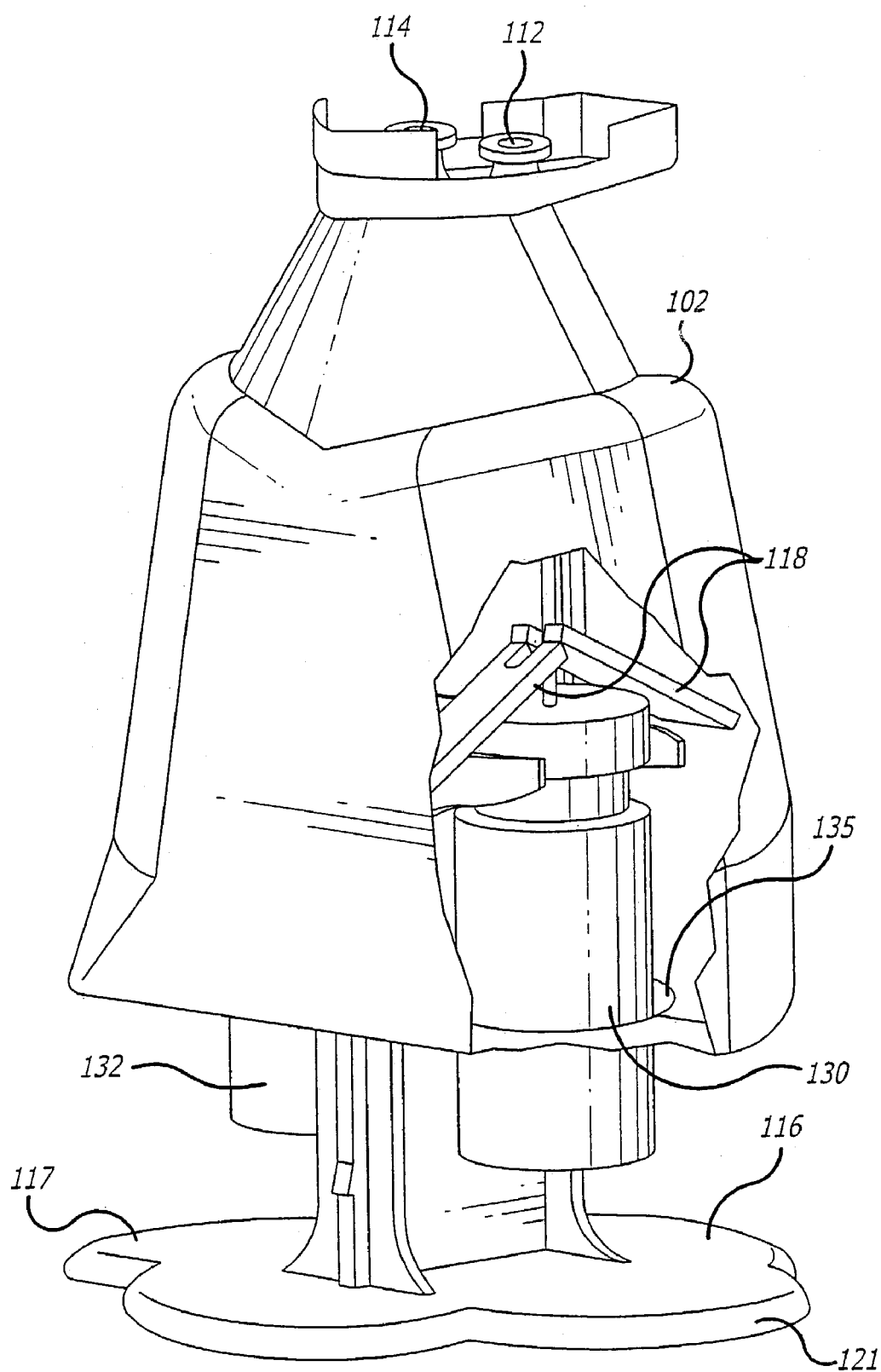
FIG. 16 is a cut away view showing the hood of the embodiment shown in FIG. 14 being lowered onto the base during assembly.

Referring to FIG. 16 which shows a view similar to that shown in FIG. 12, hood 102 is provided internally with rounded jaws 131 and 133 (not shown) which firmly clasp the tops of vials 130 and 132. Jaws 131 and 133 suspend vials 130 and 132 in carved rounded recesses 135 and 139 (not shown). The inside of the jaw has a part circular horizontal ledge where the bottle can sit vertically. Jaws 130 and 132 and recesses 135 and 139 maintain vials 130 and 132 in a vertical position prior to tilting as recesses 135 and 139 prevent tilting until the bottom of each vial is above the recesses. Arms 103 and 107 are vertically positioned and have a resilient flexibility to engage and tip vials 130 and 132 and the vials tilt after the hood clasps the bottoms of the vials. Base 116 is shaped to provide visual guides 117 and 121 to assist the user in visually matching the round and square portion of hood 102 and base 116 for alignment and proper orientation. Once assembled hood 102 is configured to snap into the base by use of snap fit members 111.

Figure 17:
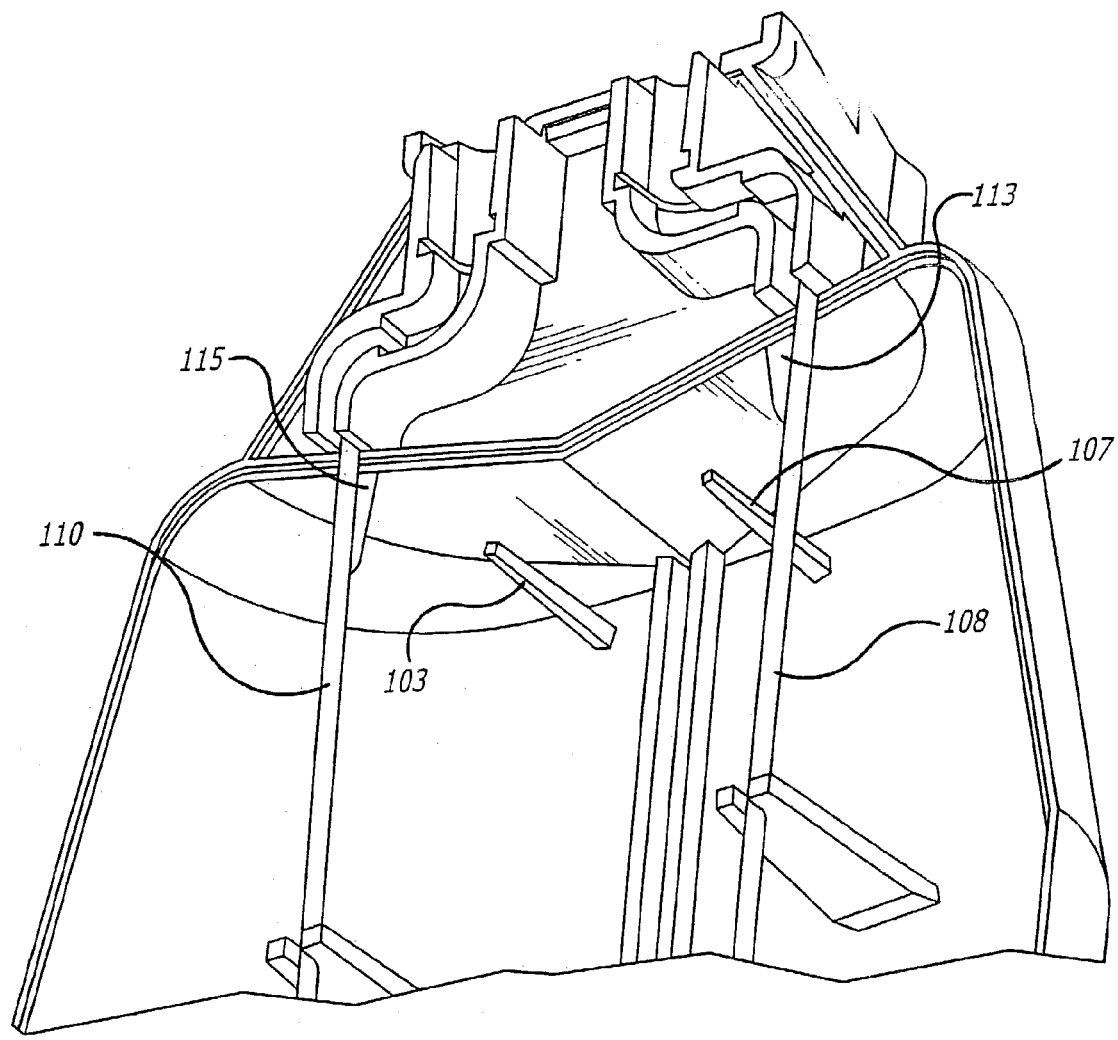
FIG. 17 is a partial cross-sectional view of the embodiment shown in FIG. 14.
Figure 18:
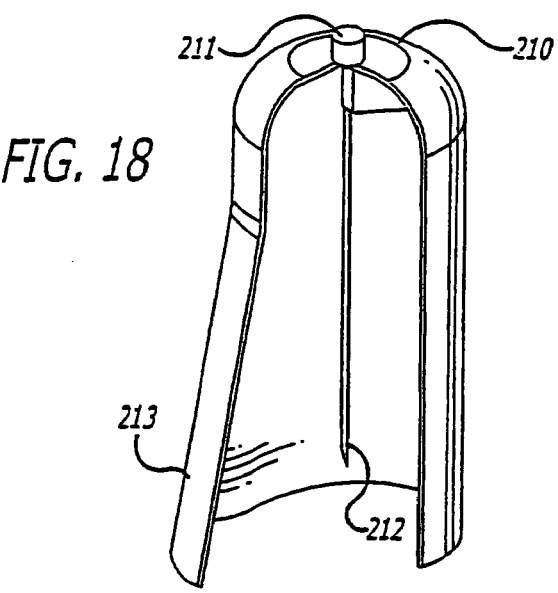
FIG. 18 is a frontal view showing a cover of an alternative embodiment of the invention for use with a single vial.
Figure 19:
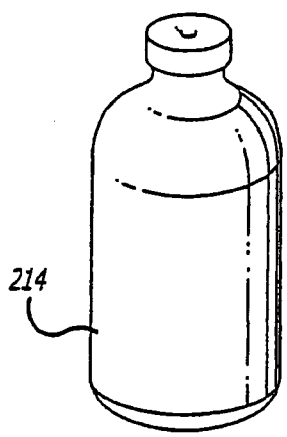
FIG. 19 is a frontal view showing the vial of the embodiment shown in FIG. 18.
Figure 20:
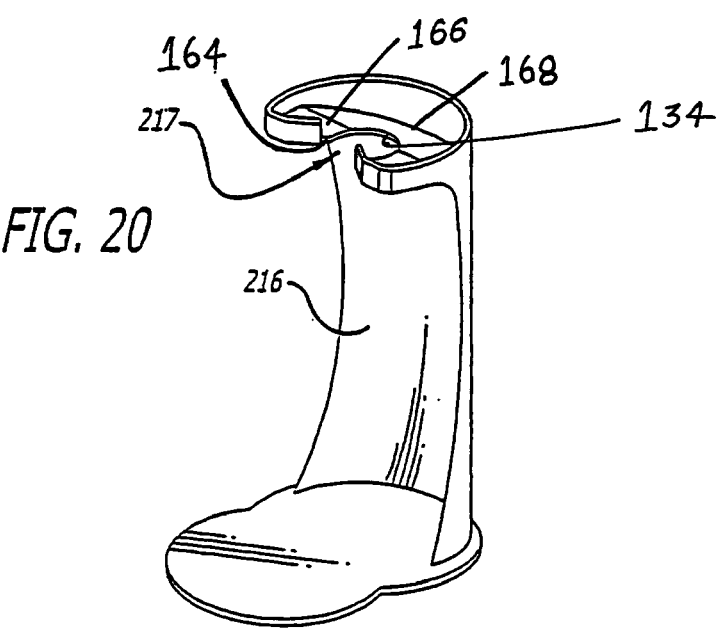
FIG. 20 is a frontal view showing the base of the embodiment shown in FIG. 18.

When using the inline body, fibrinogen and thrombin typically take up only a small portion of the volume of the vial. With most of the vial being empty, depressurization is not a problem. Therefore, venting is not usually necessary. However, most medical personnel are used drawing out a desired volume of liquid from a vial by first injecting the same volume of sterile air into the vial. Then the syringe automatically withdraws the same amount of liquid volume to equalize the pressure in the vial. However such pressurization may cause problems in that fluids may back up into the needles prematurely. Additionally, this method also causes air bubbles and inaccurate dosages. Accordingly, venting is desirable to prevent such undesired pressurization and release unwanted air while maintaining the sterile field. To address this issue, an oversized piece of hypo tube can be used to provide a collar over the needle which has an inner diameter of 0.002 in greater than the outer diameter of the needle. When the needle pushes against the collar, it makes a gap allowing air to escape between the needle and collar. Alternatively as shown in FIG. 17, a pair of dagger-like molded inserts 113 and 115 alongside each needle which is against drawing tubes 108 and 110 which allow air to escape within the sterile field. If desired inserts 113 and 115 may be provided with sharply pointed tips or cutting edges to create a hole alongside the needles which stays open after piercing. The hole allows air but not liquid to escape.

Although only two bottles are depicted for use with the inventive filling device, adaptation can be easily made to allow the use of three or more, which can directly fill three or more reservoirs contained within the applicator. This adaptation can be accomplished by expanding the hood and adding another inlet port, transverse channel and drawing tube.

During surgery, it is desirable to have access to variable doses of intravenous drugs. However, due to the limitations of the operating theater, syringes are often pre-filled in a separate room under a hood which maintains the sterile field. Current practice for dispensing local anesthetic or saline during surgery is to reach in and out of the sterile field to get more fluids or to dump the fluid into a sterile bowl inside the sterile field. This practice raises the risk of needle sticks, contamination or misuse of a non-labeled fluid in the sterile field.

Referring to FIGS. 18 to 22, an alternative embodiment of the inventive device is shown in the form of a single vial, direct filling device 200 having a cover 210 which snaps onto a base 216 thereby enclosing the vial 214 within the structure, allowing device 200 to be brought into a sterile field. This device provides needleless filling of fluids from non-sterile vials inside the sterile field with reduced waste, while maintaining label visibility for application safety. The device consists of a base or bag, cover and a needle. With this device the vial is completely shrouded and can be moved into the sterile field. The device is for single use, but multiple fillings. It is understood that the system may come with a needle, tube, and/or other structures for mating with the syringe such as in accordance with one of the embodiments described above, with one example being shown in FIG. 22A which, where indicated, identifies similar structures with identical numbers as used with previous embodiments, or, alternatively, the syringe may be attached to a needle retracted within a protective cover so that the needle is only exposed within the sterile environment of the system.

Figure 21:
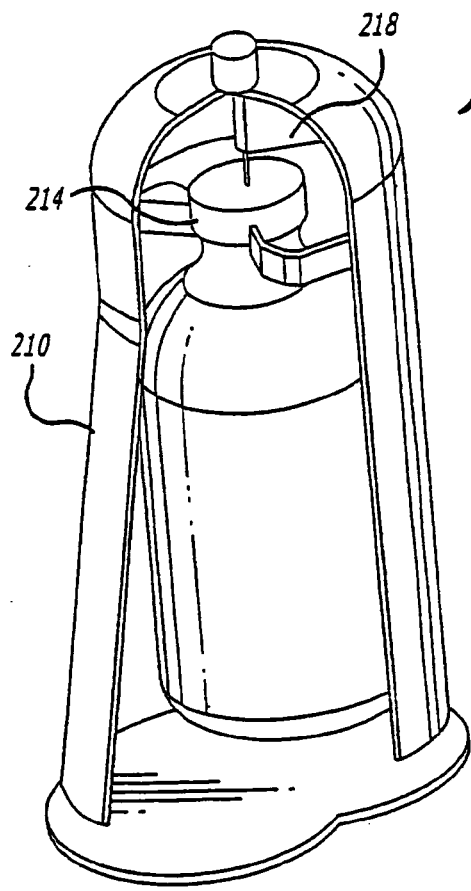
FIG. 21 is a frontal view showing the assembled system of the embodiment shown in FIG. 18 before engagement.
Figure 22A:
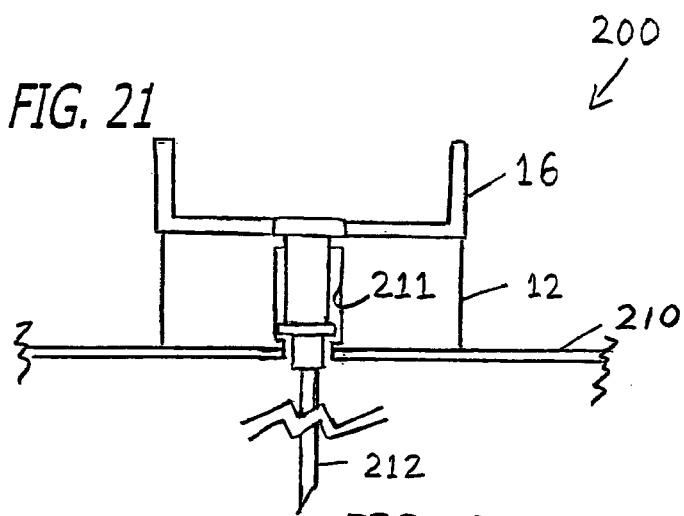
FIG. 22A is an enlarged side elevational view of the embodiment shown in FIG. 22, with portions of the device cut away.
Figure 22:
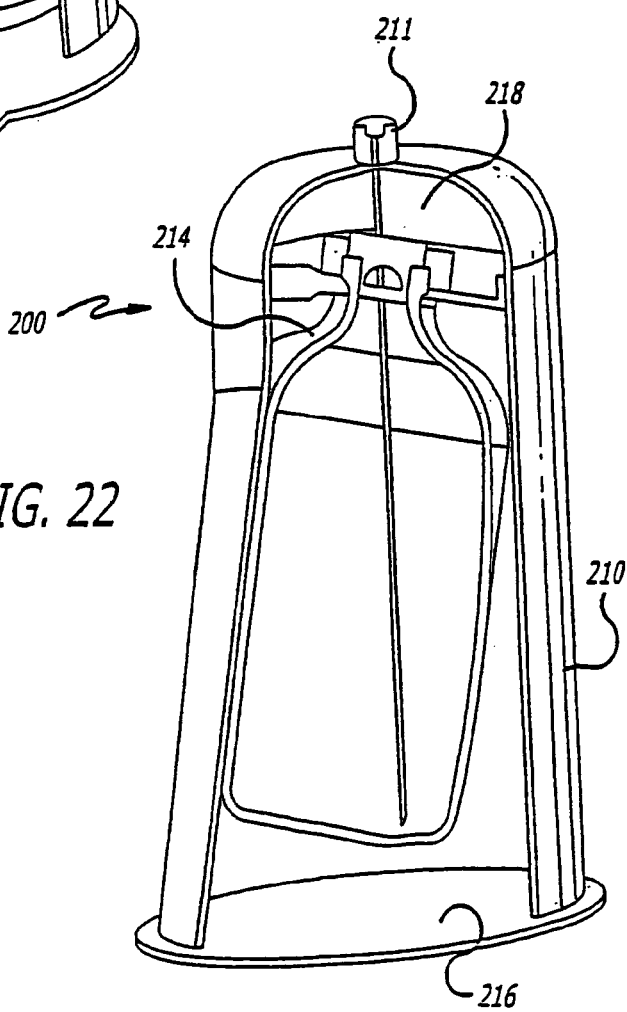
FIG. 22 is a frontal view showing the assembled system of the embodiment shown in FIG. 18 after engagement.

Cover 210 has a hole 211 which receives needle 212 and has a tilted side portion 213 which accommodates vial 214 tilting. Base 216 has a curved notch 217 where the neck of vial 214 rests. Vial 214 may be any standard size vial which is used for intravenous medication. Vial 214 is loaded into the device and is suspended by its neck. This arrangement accommodates multiple vial sizes and tilting of vial 214. FIG. 21 shows the assembled system 200 with vial 214 sitting in base 216 in vertical position. Rib 218 is tilted before engagement. FIG. 22 shows the device after it is fully assembled and with rib 218 fully engaged. Cover 210 has a feature that tilts the vial 214 for maximum fluid removal. This can be achieved while device 200 is sitting on a table in an upright position. When fully assembled the non-sterile vial 214 is shrouded and can be brought inside the sterile field providing a revisitable supply of medical fluid to the user. Both cover 210 and base 216 are preferably clear to allow for visual inspection of the vial label and fluid level.

Figures 23, 24:
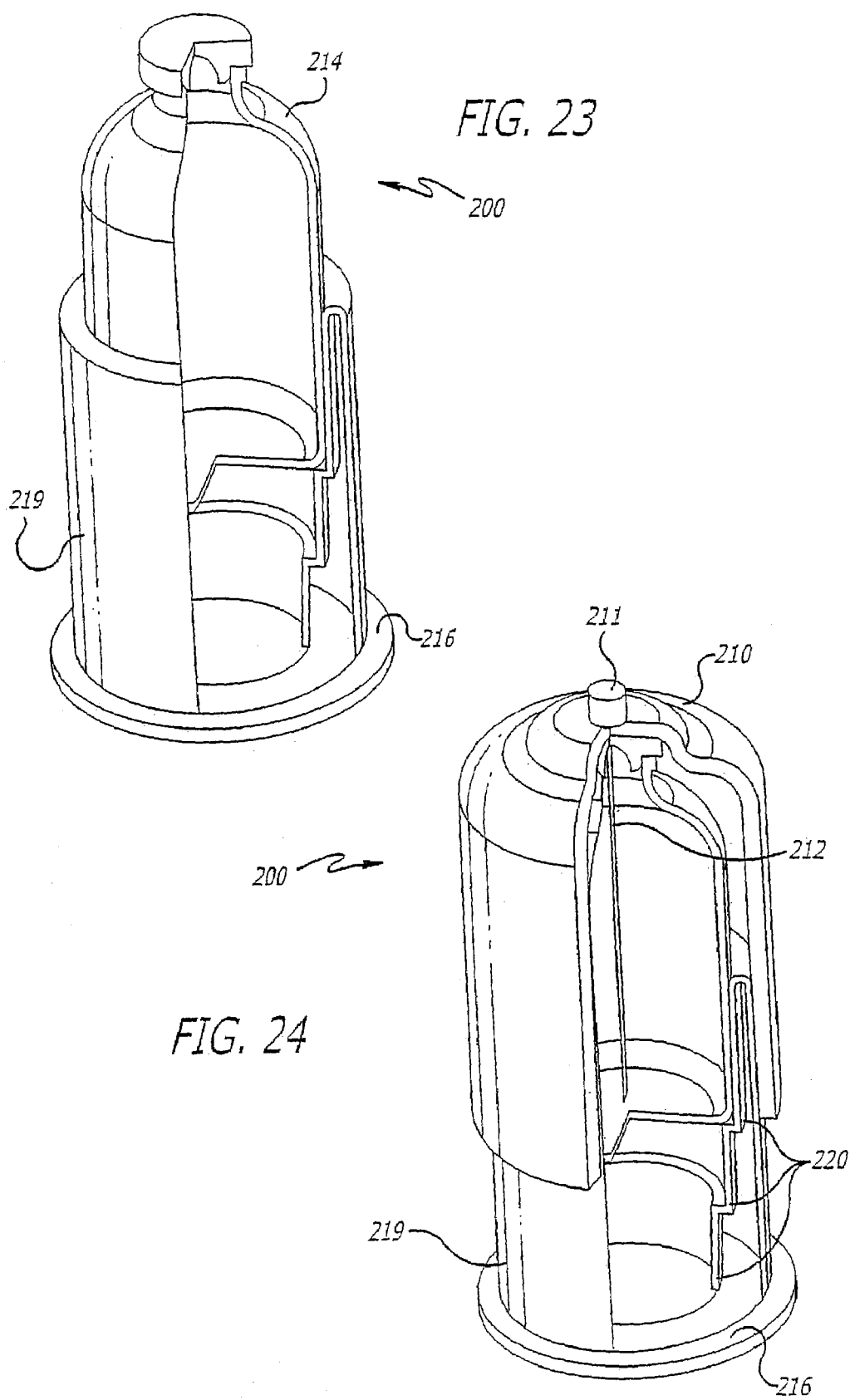
FIG. 23 is a frontal view showing the assembled system without the cover of an alternative embodiment of a single vial system of the invention.
FIG. 24 is a frontal view showing the system with the cover of the embodiment shown in FIG. 23.

FIGS. 23 & 24 show an alternative embodiment of filler device 200 where the syringe can be filled in an upright position while sitting on a table. Filler device 200 does not tilt vial 214, but instead has needle 212 extending completely to the bottom of vial 214. More specifically, FIG. 23 shows the inventive device before cover 210 is assembled to it. As shown in FIG. 24, in preferred embodiments, the inventive device 200 further comprises locking rings 219 and mating receptacles 220 to accommodate different vial sizes.

Figure 25:
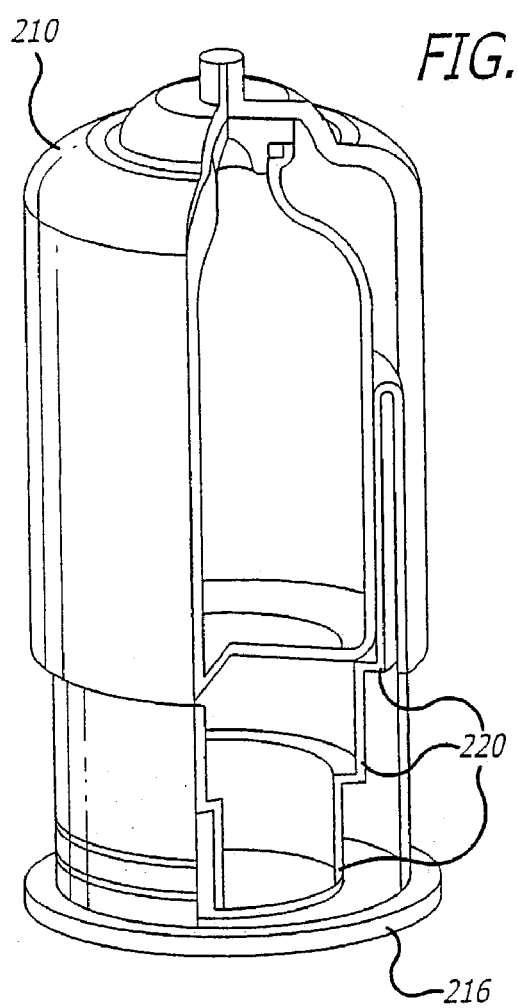
FIG. 25 is a frontal view showing the assembled system of an alternative embodiment of a single vial system of the invention.
Figure 26:
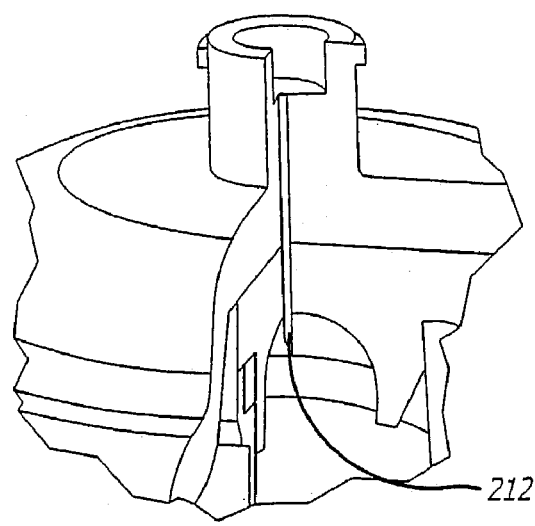
FIG. 26 is a frontal view showing a detailed view of the cover and needle assembly of the embodiment shown in FIG. 25.

FIGS. 25 & 26 show an alternative embodiment of the device shown in FIGS. 23 and 24. Needle 212 is a short needle which extends just past the septum into vial 214. The device is then inverted for filling the syringe. This embodiment would be useful for withdrawing small volumes of fluid as a longer needle extending to the bottom of the vial may withdraw air instead of liquid. Inversion of the vial is often desirable for withdrawing suspensions.

Figure 27:
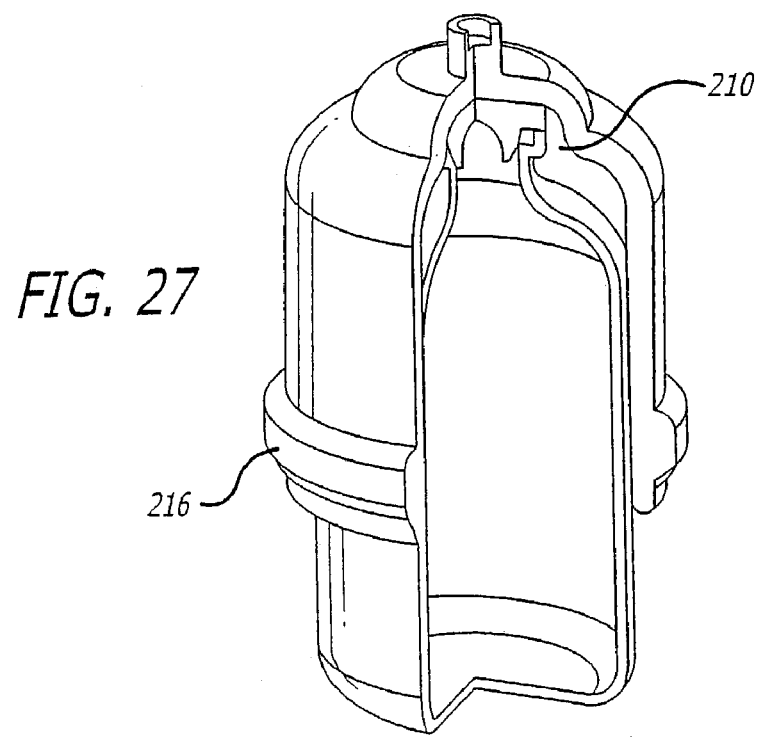
FIG. 27 is a frontal view showing the assembled system of an alternative embodiment of a single vial system of the invention.

FIG. 27 shows an alternative embodiment of the device shown in FIGS. 25 and 26. However, in this embodiment, a plastic bag is used as base 216. More specifically the base 216 comprises a plastic bag that is attached to the cover 210. When vial 214 is assembled the bag is unrolled and sealed with an adhesive strip. Cover 210 locks vial 214 into place.

While illustrative embodiments of the invention have been described above, it is, of course, understood that various modifications will be apparent to those of ordinary skill in the art. Many such modifications are contemplated as being within the spirit and scope of the invention.

The invention claimed is:

1. A connector for connecting a fluid dispensing instrument to a single container of fluid having a longitudinal axis, the connector comprising:
   a) a body having a bottom and a top, said top having an outer perimeter and an outlet port within said perimeter, said bottom having an inlet port connected to said outlet port wherein said inlet port is connected to said outlet port by a bore in said body;
   b) a collar extending from said perimeter, said collar being adapted to detachably receive said dispensing instrument;
   c) a tube is connected to said inlet port and having an end distal to said inlet port for extending into said container, said end having an opening for drawing fluid; and
   d) a hood extending from said body and including a base, an exterior surface, and a support surface extending inwardly from the exterior surface and above the base; said support surface having a generally laterally extending slot relative to the longitudinal axis, said slot slidably and releasably receiving a neck of said single container, said hood having a length sufficient to enclose the container when received by said support surface such that once the container is received within said hood, fluid in the container can be drawn into said dispensing instrument through the distal end of the tube and the connector substantially encloses the container.

2. The connector as recited in claim 1 wherein said collar, said body, and said hood are formed of thermoplastic materials.

3. The connector as recited in claim 2 wherein said thermoplastic is selected from the group consisting of polycarbonate, polystyrene, polypropylene, polytetrafluoroethylene, acrylonitrile butadiene-styrene, and acrylic.

4. The connector as recited in claim 1 wherein said collar, said body, and said hood are formed as a single thermoplastic member.

5. The connector as recited in claim 1 wherein said tube is formed of a metallic material.

6. The connector as recited in claim 1 wherein said collar is keyed to said dispensing instrument such that said dispensing instrument may be fitted to said connector in only one orientation.

7. The connector as recited in claim 1 wherein said hood comprises a resilient material and is sized such that when said container is positioned within said hood, said hood resiliently conforms to fit and secure said container in place.

8. The connector as recited in claim 1 wherein said hood further comprises a locking member adapted to secure said container to said connector.

9. The connector as recited in claim 8 wherein said locking member comprises resilient plastic joined to said hood and extends radially inward from said hood such that when said container is positioned within said locking member, said locking member secures said container in place.

10. The connector as recited in claim 8 wherein said locking member is an o-ring fitted within said hood.

11. The connector as recited in claim 1 wherein said outlet port comprises a circular shape.

12. The connector as recited in claim 1 wherein said bore is tapered.

13. The connector as recited in claim 1 wherein said collar is capable of making a Luer lock with said dispensing instrument.

14. The connector as recited in claim 1 wherein said connector further comprises a tubular air vent attached to said connector wherein said air vent further comprises a first opening, a second opening, and a conduit connecting said first opening to said second opening and said first opening is positioned such that when said container is locked to said hood, said first opening is situated inside said container and said second opening is externally situated on said connector such that positive air pressure is supplied said container reducing any vacuum forces created within said container during drawing.

15. The connector as recited in claim 1 wherein said distal end of said tube has a pointed tip adapted to sealably pierce a cap of said container.

16. The connector as recited in claim 1 wherein said hood is adapted to allow the container to tilt relative to the connector.

17. A connector for connecting a fluid dispensing instrument to a single container of fluid comprising:
   a) a body having a bottom and a top, said top having an outer perimeter and an outlet port within said perimeter, said bottom having an inlet port connected to said outlet port wherein said inlet port is connected to said outlet port by a bore in said body;
   b) a collar extending from said perimeter, said collar being adapted to detachably receive said dispensing instrument;
   c) a tube is connected to said inlet port and having an end distal to said inlet port for extending into said container, said end having an opening for drawing fluid; and
   d) a hood extending from said body and including a base, an exterior surface, and a support surface extending inwardly from the exterior surface and above the base; said support surface adapted to slidably and releasably receive said single container, and adapted to support the single container suspended above at least a portion of the base, said hood having a length sufficient to enclose the container when received by said support surface such that once the container is received within said hood, fluid in the container can be drawn into said dispensing instrument through the distal end of the tube and the connector substantially encloses the container.

18. A connector for connecting a fluid dispensing instrument to a single container of fluid comprising:
  a) a body having a bottom and a top, said top having an outer perimeter and an outlet port within said perimeter, said bottom having an inlet port connected to said outlet port wherein said inlet port is connected to said outlet port by a bore in said body;
  b) a collar extending from said perimeter, said collar being adapted to detachably receive said dispensing instrument;
  c) a tube is connected to said inlet port and having an end distal to said inlet port for extending into said container, said end having an opening for drawing fluid; and
  d) a hood extending from said body and including a base, an exterior surface, and a support surface extending inwardly from the exterior surface and above the base; said support surface adapted to slidably and releasably receive said single container, and adapted to support the single container suspended above at least a portion of the base in a tilted position relative to the connector, said hood having a length sufficient to enclose the container when received by said support surface such that once the container is received within said hood, fluid in the container can be drawn into said dispensing instrument through the distal end of the tube and the connector substantially encloses the container.

19. The connector of claim 17 wherein the single container is suspended above an underside of the base.

20. The connector of claim 1 wherein the support surface is a first support surface and the hood further includes a second support surface which extends radially inward from the exterior surface and is spaced below the first support surface.

21. The connector of claim 17 wherein said collar, said body, and said hood are formed of thermoplastic materials.

22. The connector of claim 17 wherein said collar, said body, and said hood are formed as a single thermoplastic member.

23. The connector of claim 17 wherein said tube is formed of a metallic material.

24. The connector of claim 17 wherein said collar is keyed to said dispensing instrument such that said dispensing instrument may be fitted to said connector in only one orientation.

25. The connector of claim 17 wherein said hood comprises a resilient material and is sized such that when said container is positioned within said hood, said hood resiliently conforms to fit and secure said container in place.

26. The connector of claim 17 wherein said hood further comprises a locking member adapted to secure said container to said connector.

27. The connector of claim 17 wherein said outlet port comprises a circular shape.

28. The connector of claim 17 wherein said bore is tapered.

29. The connector of claim 17 wherein said collar is capable of making a Luer lock with said dispensing instrument.

30. The connector of claim 17 wherein said connector further comprises a tubular air vent attached to said connector wherein said air vent further comprises a first opening, a second opening, and a conduit connecting said first opening to said second opening and said first opening is positioned such that when said container is locked to said hood, said first opening is situated inside said container and said second opening is externally situated on said connector such that positive air pressure is supplied said container reducing any vacuum forces created within said container during drawing.

31. The connector of claim 17 wherein said distal end of said tube has a pointed tip adapted to sealably pierce a cap of said container.

32. The connector of claim 17 wherein said hood is adapted to allow the container to tilt relative to the connector.

33. The connector of claim 17 wherein said support surface is inclined to support the container in a non-vertical position.

34. The connector of claim 1 wherein said support surface is inclined to support the container in a non-vertical position.

* * * * *

UNITED STATES PATENT AND TRADEMARK OFFICE
CERTIFICATE OF CORRECTION

PATENT NO. : 7,207,969 B2
APPLICATION NO. : 10/309338
DATED : April 24, 2007
INVENTOR(S) : Gordon H. Epstein et al.

It is certified that error appears in the above-identified patent and that said Letters Patent is hereby corrected as shown below:

On Title Page, Item (63) Related U.S. Application Data, delete "Continuation-in-part of application No. 09/307,056, filed on May 7, 1999, now Pat. No. 6,475,183" and insert -- This application is a continuation of application no. 09/456,728, filed on December 8, 1999, now Pat. No. 6,488,650 which is a continuation-in-part of application no. 09/307,056, filed on May 7, 1999, now Pat. No. 6,475,183, which claims the benefit of provisional application no. 60/087,856 filed June 3, 1998. --

Column 1, line 7, delete "This application is a continuation-in-part of copending U.S. patent application Ser. No. 09/307,056, filed on May 7, 1999, to Epstein et al, now issued U.S. Pat. No. 6,475,183, the subject matter of which is hereby incorporated by reference." and insert -- This application is a continuation of application number 09/456728, filed December 8, 1999, which is a continuation-in-part of application number 09/307056, filed May 7, 1999 which claims the benefit of provisional application serial number 60/087856, filed June 2, 1998, the disclosures of which applications are hereby incorporated herein by reference thereto. --

Signed and Sealed this

Sixteenth Day of September, 2008

JON W. DUDAS
*Director of the United States Patent and Trademark Office*